(12) United States Patent
McKim et al.

(10) Patent No.: US 6,998,249 B1
(45) Date of Patent: Feb. 14, 2006

(54) TOXICITY SCREENING METHOD

(75) Inventors: James M. McKim, Kalamazoo, MI (US); Gary L. Cockerell, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/586,242

(22) Filed: Jun. 2, 2000

Related U.S. Application Data
(60) Provisional application No. 60/156,206, filed on Sep. 27, 1999.

(51) Int. Cl.
*C12Q 1/02* (2006.01)

(52) U.S. Cl. ........................................................ 435/29
(58) Field of Classification Search .................... 435/29
See application file for complete search history.

(56) References Cited

U.S. PATENT DOCUMENTS 4,882,270 A    11/1989   Moroz ............................ 435/7

FOREIGN PATENT DOCUMENTS

| DK | 171085 | 6/1994 |
| GB | 2271772 A | 4/1994 |
| WO | WO 95/32184 | 11/1995 |
| WO | WO 95/35278 | 12/1995 |
| WO | WO 97/49653 | 12/1997 |

OTHER PUBLICATIONS

Renwick et al., Regulatory and Pharmacology 18: 463–480 (1993).*
Eisenbrandt et al., Fd. Chem. Toxic. 32(7): 655–669 (1994).*
Generaly & Applied Toxicology, vol. I, Stockton Press, New York, 1993, pp. 11–20.*
Fricker, Toxic. In Vitro 8(4): 879–881 (1994).*
Yao et al., Toxicology Methods 2(3): 199–218 (1992).*
Chung et al., Chonnam J Med Sci 1(2): 128–138 (1988).*
Morrison et al., Biomaterials 16(13): 987–992 (Sep. 1995).*
Garza–Ocanas et al., Toxicology 73(2): 191–201 (1992).*
Yao et al., Toxicology Methods (2):3: 199–218 (1992). Abstract.*
Chung et al., Chonnam J Med Sci 1(2): 128–138 (1988). Abstract.*
Morrison et al., Biomaterials 16(13): 987–992 (Sep. 1995). Abstract.*
Garza–Ocanas et al., Toxicology 73(2): 191–201 (1992). Abstract.*
Connors et al. (Biochem Pharmacol 24:2217–24), 1975.*
Burkhardt, John E. et al., "Commentary: A View on Discovery Pathology," *Toxicologic Pathology*, 27(4):472–473 (1999).

Car, B.D. et al., "Commentary: Discovery Toxicology—A Nascent Science," *Toxicologic Pathology*, 27(4):481–483 (1999).
Cockerell, Gary L. et al., "Focus On: Discovery Pathology," *Toxicologic Pathology*, 27(4):471 (1999).
Cockerell, G.L. et al., "Commentary: Redesigning the Preclinical Paradigm: The Role of Pathology and Toxicology in Supporting Discovery Research," *Toxicologic Pathology*, 27(4):477–478 (1999).
Denizot, F. et al., "Rapid colorimetric assay for cell growth and survival Modifications to the tetrazolium dye procedure giving improved sensitivity and reliability," *J. Immunol. Methods.* 89:271–277 (1986).
Drug Discovery Using CombiChem's *Drug Discovery Engine™*, http://www.combichem.com/Publication/Papers/Discovery.htm, pp. 1–6 (1997).
Essig–Marcello, J. et al., "A Double–Label *In Situ* Cytotoxicity Assay Using the Fluorescent Probes Neutral Red and BCECF–AM," In vitro *toxicol*, 3(3):219–227 (1990).
Feinfeld, D.A. et al., "Urinary Glutathione–S–Transferase in Cisplatin Nephrotoxicity in the Rat," *J Clin Chem Clin Biochem.* 24:529–532 (1986).
Goegan, P. et al., "Effects of Serum Protein and Colloid on the AlamarBlue Assay in Cell Cultures," *Toxicol. In Vitro* 9(3):257–266 (1995).
Harleman, J.H., "Commentary Contribution of Pathology to Drug Research and Development in the Next Decade," *Toxicologic Pathology*, 27(4):479–480 (1999).
Kangas, L. et al., "Bioluminescence of Cellular ATP: A New Method For Evaluating Cytotoxic Agents In Vitro," *Med Biol*, 62:338–343 (1984).
Lowik, C.W.G.M. et al., "Quantification of Adherent and Nonadherent Cells Cultured in 96–Well Plates Using the Supravital Stain Neutral Red," *Anal. Biochem.* 213:426–433 (1993).
Mosmann, T., "Rapid Colorimetric Assay for Cellular Growth and Survival: Applicaiton to Proliferation and Cytotoxicity Assays," *J. Immunol. Methods,* 65:55–63 (1983).
Myers, P.L., "Re–enginering Of The Drug Discovery Process, Utilising A Unique Combination Of Library Design And Parallel Synthesis," http://combichem.com/Publication/Papers/reenginering.htm, pp. 1–4 (1997).
Oberley, T. et al., "Effects of Lead Administration on Developing Rat Kidney II. Functional, Morphologic, and Immunohistochemical Studies," *Toxicol. Appl. Pharmacol.* 131:94–107 (1995).

*Primary Examiner*—Jean C. Witz
(74) *Attorney, Agent, or Firm*—Austin W. Zhang

(57) ABSTRACT

The present invention provides materials and methods for predicting the in vivo toxicity of a given compound. For example, the invention comprises conducting at least three distinct assays in parallel to provide information about three distinct parameters of cytotoxicity of a chemical in a given target cell, which information is useful for predicting in vivo cytotoxicity.

24 Claims, 13 Drawing Sheets

OTHER PUBLICATIONS

Redick, J. et al., "Immunohistochemical Localization of Glutathionhe S–Transferases in Livers of Untreated Rats," *J. Biol. Chem,* 257:15200–15203.

Roehm, N. et al., "An improved colorimetric assay for cell proliferation and viability utilizing the tetrazolium salt XTT," *J. Immunol. Methods,* 142:257–265 (1991).

Ryan, Anne M., "Commentary: Role of the Pathologist in the Identification and Characterization of Therapeutic Molecules," *Toxicologic Pathology,* 27(4):474–476 (1999).

The Universal Informer Library™: An Update, http://www.combichem.com/Publication/Papers/Train.htm, pp. 1–5 (1997).

Jung, et al., "Multiple Peptide Synthesis Methods and Their Applications", *angew Chem. Int. ed. Engl.,* 31:367–383 (1992).

Ellman and Bunin, *J. Amer. Chem. Soc.,* 114:10997 (1992).

DeWitt, et al., "Diversomers": An approach to nonpeptide, nonoligomeric chemical diversity, *Proc. Nat'l. Acad. Sci.,* 90:6909 (1993).

Pavia, et al., "The Generation of Molecular Diversity", *Bioorg. Med. Chem. Lett.,* 3:387–396 (1993).

De Angelis, I. et al., "Established cell lines for safety assessment of food contaminants: differing furazolidone toxicity to V79, HEp–2, and CACO–2 cells," *Fd. Chem. Toxic.,* 32(5):481–488(1994).

Elmore, Eugene et al., "The human epithelial cell cytotoxicity assay for determining tissue specific toxicity," *Methods in Cell Science,* 22:17–24(2000).

Klostergaard, Jim et al., "Tomoricidal effector mechanisms of murine *Bacillus Calmette–Guerin*–activated macrophages: mediation of cytolysis, mitochondrial respiration inhibition, and release of intracellular iron by distinct mechanisms," *Cancer Research,* 47:2014–2019(1987).

Steinbach O.M. and Wolterbeek H.Th., "Effects of copper on rat hepatoma HTC cells and primary cultured rat hepatocytes," *J. Inorg. Biochem.,* 53:27–48(1994).

Walum, E. et al., "Cellular methods for identification of neurotoxic chemicals and estimation of neurotoxicological risk," *Neurotoxicology,* 7(4):321–326(1993).

Wataha, J.C. et al., "The in vitro effects of metal cations on eukaryotic cell metabolism," *J. Biomed. Mater. Res.* 25:1133–1149(1991).

Jensen, M.T. et al., "Microbial production of skatole in the hind gut of pigs fed different diets and its relation to skatole deposition in backfat", Proc of Meeting of EAAP Working Group, Meat & Livestock Comm., UK, Sep. 27–29, 1995.

Babol, J. et al., "Involvement of cytochrome P450IIE1 in hepatic metabolism and clearance of skatole", EEAP Pub. No. 92, pp. 49–53. Oct. 1–3, 1997.

Babol, J. et al., "Relationship between oxidation and conjugation metabolism of skatole in pig liver and levels of skatole in fat", EEAP Pub. No. 92, pp. 54–57. Oct. 1–3, 1997.

Laue, A. et al., "Effect of tryptophan infusion on the production of indole derivatives in the hind gut and absorption to the portal vein", EEAP Pub. No. 92, pp. 58–61. Oct. 1–3, 1997.

Babol, J. et al., "Relationship between metabolism of androstenone and skatole", EEAP Pub. No. 92, pp. 62–65. Oct. 1–3, 1997.

Edwards, S.M. et al., "Involvement of cytochrome b5 in androstenone biosynthesis", EEAP Pub. No. 92, pp. 66–69. Oct. 1–3, 1997.

Andersson, K. et al., "Relations between boar taint and puberty in entire pig males", EEAP Pub. No. 92, pp. 70–73. Oct. 1–3, 1997.

Lundström, K. et al., "Skatole levels in pigs selected for high lean tissue growth rate on different dietary protein levels", Livestock Prod Sci, vol. 38, pp. 125–132, 1994.

Baek, C. et al., "Identificaiton of Selected Metabolites of Skatole in Plasma and Urine from Pigs", J Agric Food Chem, vol. 45, pp. 2332–2340, 1997.

Babol, J, et al., "Relationship Between Oxidation and Conjugation Metabolism of Skatole in Pig Liver and Concentrations of Skatole in Fat", J Anim Sci, vol. 76, pp. 829–838, 1998.

Babol, J. et al., "Hepatic Metabolism of Skatole in Pigs by Cytochrome P4502EI", J Anim Sci, vol. 76, pp. 829–838, 1998.

Squires, E.J. et al., "Relationship Between Cytochrome P450IIE1 in Liver and Levels of Skatole and Its Metabolites in Intact Male Pigs", J Anim Sci, vol. 75, pp. 2506–2511, 1997.

Claus, R. et al., "Oestrogens, compared to other steroids of testicular origin, in bloodplasma of boars", Acta Endocrino, vol. 94, pp. 404–411, 1980.

Friis, C., "Is boar–taint related to sex differences or polymorphism of skatole metabolism", Proc of Meeting of EAAP Working Group, Meat & Livestock Comm., Sep. 27–29, 1995.

* cited by examiner

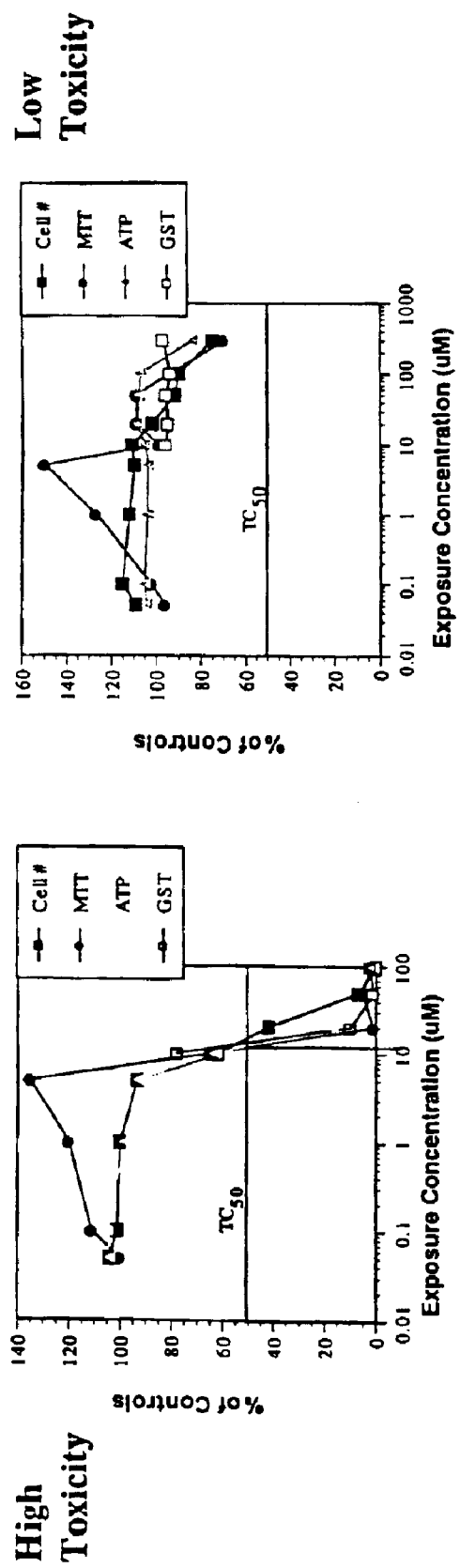
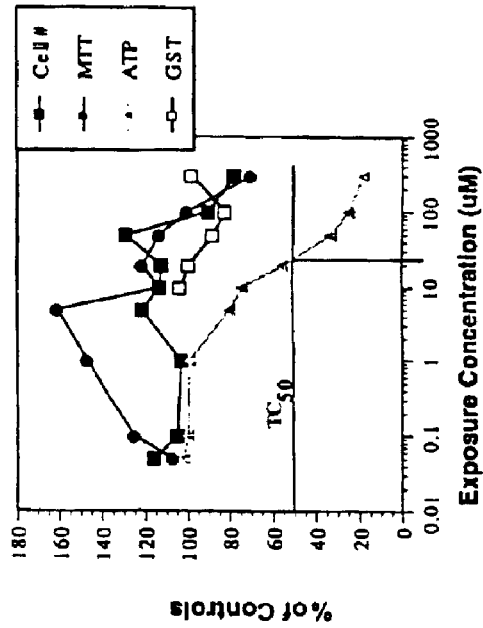
FIG. 10 Low Toxicity
FIG. 9 High Toxicity
FIG. 11 Potentially Toxic Unique Mechanism

**High toxicity *in vivo***

**Low toxcity *in vivo***

TOXICITY SCREENING METHOD

The present application claims priority to United States provisional application entitled "Improved Toxicity Screening Method" filed on Sep. 27, 1999 and given the Ser. No. 60/156,206. The entire text of the aforementioned disclosure is incorporated herein by reference without prejudice or disclaimer.

FIELD OF THE INVENTION

The present invention describes novel in vitro methods for predicting in vivo toxicity of chemical compounds, understanding the relative toxicity of drug candidates, and identifying mechanisms of toxicity.

BACKGROUND OF THE INVENTION

The process of identifying a new drug candidate is long and tedious with many promising compounds eliminated from development during preclinical toxicity testing in animals. One reason for the high number of drop out compounds during the preclinical phase is the lack of useful toxicity data early in the discovery program. Many pharmaceutical companies have recognized this in the last 2 to 3 years [Cockerell et al., Toxicol. Path. vol 27, no. 4, p 471, (1999); Burkhardt et al., Toxicol. Path. vol 27, no. 4, p 472–473 (1999); Ryan, Toxicol. Path. vol 27, no. 4, p 474–476 (1999); Cockerell et al., Toxicol. Path. vol 27, no. 4, p 477–478, (1999)].

To date in vivo toxicity of a given candidate substance as a potential drug has involved the use of animal models. Underlying the animal tests is the assumption that the effects that agents produce in animals are applicable and predictive of effects in humans. In general, when the dosage is based on a per unit of body surface area, toxicology data from animals is applicable to humans. On the other hand, when the dosage is based on animal body weight, humans are more susceptible to toxicity than the test animals. Nevertheless, the vast majority of drugs are developed to be given on the basis of body weight.

Additionally, the actual numbers of animals used in drug testing are much lower than the human population likely to be exposed to the drug. For example, a 0.01% incidence of human exposure to a given drug means that approximately 25,000 out of 250 million individuals are exposed to a drug. To detect such a low incidence in animals would require that 30,000 animals be exposed to the drug. This is clearly an impractical number considering the variety of drugs in development at any given time. Consequently, exposure of fewer animals to high doses of candidate substances is desirable to identify hazards to humans exposed to low doses.

The use of animals in the initial stages of drug development is an expensive and inefficient method of producing toxicological data for new drugs especially in light of the fact that most chemicals this early in development will not be considered drug candidates. Various companies have tried to employ other methods of toxicological screening before the putative drugs enter the arena of animal testing.

A common approach to solving the toxicology data deficit has been to incorporate in vitro toxicity testing of promising new drugs into the drug discovery process at a time when new compounds are being identified for potency and efficacy against therapeutic targets. Quality toxicity data at this early stage permits pharmaceutical chemists to attempt to "design out" toxicity while maintaining efficacy/potency. Although this is a good idea in principle, in practice it has been extremely difficult to develop robust in vitro toxicity data and to match in vitro data with in vivo toxicity.

Key issues have been deciding on the type and nature of assays to be utilized and the test system to be employed. There are many biochemical and molecular assays that claim to assess toxicity in cells grown in culture. However, when only one or even two assays are used over a limited range of exposure concentrations, the probability of false negative and false positive data is high. Some of the most commonly used assays include, but are not limited to, leakage of intracellular markers as determined by lactate dehydrogenase (LDH), glutathione S-transferase (GST), and potassium, and the reduction of tetrazolium dyes such as MTT, XTT, Alamar Blue, and INT. All have been used as indicators of cell injury. In all cases, the screens typically only involve the use of one or two endpoints. The resulting data provides a yes/no or live/dead answer. This minimalist approach to the toxicity-screening problem has resulted in little progress towards developing a robust screening system capable of providing a useful toxicity profile that has meaning for predicting similar toxicity in animals. Therefore, there remains a need in the art for the development of new screening systems that provide more useful toxicity information, especially toxicity information that can be obtained rapidly and cost-effectively at early stages of the drug discovery process. A need exists for toxicity screening systems that do not require the use of animals but that provide reliable information on relative toxicity, mechanism of toxicity, and that effectively predict in vivo toxicity.

SUMMARY OF THE INVENTION

The present invention describes significant improvements to the toxicity screening process which are embodied in numerous materials and methods described herein. These improvements provide a toxicity profile with considerable mechanistic information that can be used to identify, design, and manufacture new drugs having limited toxicity and use the drugs to treat diseases and/or disease symptoms. The process has been termed "Cluster Analysis Toxicity Screening" or "CATS" and involves monitoring several biochemical or molecular endpoints for each test compound, in a cluster of assays. The resulting data provide a profile of biochemical alterations that give much more than a live/dead answer. In addition, the redundancy built into the approach greatly reduces false positive and false negative answers. Moreover, by designing different tiers of clusters it is possible to evaluate many aspects of cellular toxicity. For example, information of relative toxicity to other compounds of the same class, and information on the mechanism of toxicity are obtained. Finally, by applying defined rules of analysis, the exposure concentration versus response curves can provide appropriate estimates of plasma concentration of a drug in vivo that would produce toxicity in liver or hematopoietic cells. As described herein CATS procedures provide improved methods for screening compounds for toxicity, and they also are incorporated into all aspects of drug identification, design, manufacture, dosing, and the like.

In one aspect, the present invention provides a method for assessing the toxicity of a compound in a living system comprising providing at least three or four multi-well culture plates, the plates containing cells and growth medium; growing the cells in said plates to a defined density; exposing the cells to a test compound after establishment of a log growth phase; and conducting at least three or four assays to ascertain the toxicity of the compound in the living test system and to create a toxicity profile for the test compound.

In a preferred embodiment, the assays are selected from a group consisting of cell cycle evaluation assays; mitochondrial function assays; energy balance assays; and cell death assays. In a further preferred embodiment, the cells used in the CATS system are derived from a rat hepatoma and are known as H4IIE cell line (ATCC Accession #CRL-1548). In yet another embodiment, the cells used in the assay are derived from a human hepatoma and are known as HepG2 cell line (ATCC Accession #HB-8065).

In another aspect, the present invention provides a method of predicting the in vivo cytotoxicity of a chemical compound comprising culturing cells in culture medium that comprises a plurality of concentrations of the chemical compound; measuring a first indicator of cell health at four or more concentrations of the chemical compound; measuring a second indicator of cell health at four or more concentrations of the chemical compound; measuring a third indicator of cell health at four or more concentrations of the chemical compound; and predicting a toxic concentration ($C_{tox}$) of the chemical compound from the measurements of the first, second, and third indicators of cell health. In a preferred embodiment, a fourth and optionally a fifth indicator of cell health also may be used. The method is much more predictive of the in vivo toxicity of the compound than if the same assays were carried out separately and independently during different phases or time periods during the drug development. This is because when a single toxicity assay is used, little information is obtained as to why the endpoint is changing, and the probability of false negative or false positive results is high, leading to incorrect decisions based on incomplete data sets.

Defining the in vitro toxicity of a chemical using a plurality of concentrations and assays allows the generation of dose response curves that can be used to determine the relative toxicity ($TC_{50}$, NOEL, and $C_{tox}$ values) and the mechanism of toxicity. The $TC_{50}$ values are used to prioritize compounds (e.g., based on relative toxicity) for additional testing and the $C_{tox}$ value is the plasma concentration in vivo that would result in toxicity estimated from the in vitro CATS analysis being tested. The test system employed will determine the types of in vivo toxicity that can be predicted. For example, where H4IIE cells are used, the data will be especially predictive of in vivo hepatic or hematopoietic toxicity.

In more particular embodiments, each of the first, second and third indicators is independently selected from the group consisting of indicators of cellular replication, indicators of mitochondrial function, indicators of intracellular energy balance, indicators of cell membrane integrity and indicators of cell mortality. Further, it is contemplated that the methods of the present invention, in addition to measuring a first, second and third indicator of cell health, also may employ more than one of a given class of indicators of cell health. For example, the method may include two or more mitogenesis assays, two or more mitochondrial function assays, two or more energy balance assays, two or more membrane integrity assays and two or more cell death assays.

In the prediction aspects of the present invention, the predicting generally comprises performing dose response analyses of measurements from the first, second, and third indicators of cell health; identifying from the dose response analyses the highest concentration of the chemical compound at which a measurable toxic effect of the chemical compound is not observable (NOEL) in any dose response analyses of the first, second, and third indicators of cell health; and selecting as $C_{tox}$ the concentration indicated by the concentration identified as NOEL. The NOEL concentration is preferably validated by measurements from at least two higher concentrations at which increased toxicity is observable with respect to one or more of the indicators of cell health. It will be appreciated that $C_{tox}$ is a predicted toxic concentration, and NOEL provides a preferred $C_{tox}$ value. Selecting a $C_{tox}$ slightly above or below the NOEL value, thereby providing a substantially equivalent $C_{tox}$, is considered to be an equivalent embodiment of the invention. In particularly preferred aspects, the predicting comprises plotting the measurements of the effect of the chemical compound on a graph as a function of concentration of the chemical component for each of the cell health indicators. In still more preferred embodiments, the measurements of the cell health indicators are displayed on a single graph. In certain embodiments, the measurements of the cell health indicators are expressed relative to a control.

As described herein, the method involves culturing cells in a plurality of concentrations of the chemical compound, so that measurements of indicators of cell health can be taken at multiple (e.g., four or more) concentrations of the chemical compound. It is desirable to have, e.g., at least about one or two lower concentrations at which the compound does not exert an apparent toxic effect with respect to an indicator of cell health. Also, with respect to at least the most sensitive indicator with which the NOEL/$C_{tox}$ value is established, it is desirable to measure the indicator at two or more concentrations greater than the $C_{tox}$ concentration. The existence of two or more measurements at concentrations greater than $C_{tox}$ serve to validate the conclusion that concentrations above $C_{tox}$ are causing a toxic effect with respect to the indicator that is being measured. A plurality of concentrations of the compound selected from a concentration range from about 0 micromolar to about 300 micromolar have been found to be useful for measuring indicators and obtaining multiple measurements at which no toxic effect is observed and also measurements at which toxic effects begin to be observed for one or more indicators. The concentration range of zero to 300 micromolar also has been found to be useful because many drugs are therapeutically effective in vivo somewhere within this concentration range. Thus, a lack of any observed toxic effects anywhere in this concentration range in a CATS analysis, combined with evidence of efficacy in this range, would be very informative in the drug development process.

In certain aspects of the invention, it is contemplated that at least one of the cell health indicators is measured from the supernatant of the cell culture. In some embodiments, it is contemplated that at least one of the cell health indicators is measured from the cellular components of the cell culture. Measuring certain indicators from cells and others from cell supernatant can improve efficiency of the CATS analysis, since such measurements can be performed in parallel, and also can potentially provide a more diverse overall indication of cell health than measurements taken solely from the cells or solely from the supernatant.

In a preferred CATS analysis, the first health indicator monitors cellular replication, the second cell health indicator monitors mitochondrial function, and the third cell health indicator monitors membrane integrity. As demonstrated in the Examples below, a CATS assay that comprises a plurality of different types of cell health indicators permits prediction of a compound's mechanism of toxicity as well as predicting concentrations at which the compound will be toxic in vivo. Thus, with respect to any of the methods described herein, one preferred variation involves a prediction of a mechanism of toxicity from the measurements of cell health (instead of, or in addition to, predicting a toxic concentration).

While three indicators of cell health provide one preferred embodiment of the present invention, it is contemplated that the CATS analysis further may comprise measuring a fourth cell health indicator selected from the group consisting of indicators of cellular replication, indicators of mitochondrial function, indicators of intracellular energy balance, indicators of cell membrane integrity and indicators of cell mortality. In addition, certain CATS analyses may further comprise measuring a fifth cell health indicator selected from the group consisting of indicators of cellular replication, indicators of mitochondrial function, indicators of intracellular energy balance, indicators of cell membrane integrity and indicators of cell mortality. Embodiments where more than five indicators are measured also are contemplated.

In certain defined embodiments, the cellular replication assay may be a cell replication assay selected from the group consisting of an assay that measures $^3$H-thymidine incorporation; a BrdU incorporation assay, PCNA expression or a CYQUANT® assay. In particularly preferred embodiments, the cellular replication assay is CYQUANT® cellular replication assay. In embodiments involving a membrane integrity assay, the membrane integrity assay is selected from the group consisting of a glutathione S-transferase assay, lactate dehydrogenase assay, aspartyl aminotransferase assay, alanine aminotransferase assay, isocitrate dehydrogenase assay, sorbitol dehydrogenase assay, glutamate dehydrogenase assay, ornithine carbamyl transferase assay, γ-glutamyl transferase assay, and alkaline phosphatase assay. A particularly preferred membrane integrity assay when using hepatic cells is a glutathione S-transferase assay. In embodiments that include a mitochondrial function assay, the mitochondrial function assay may be selected from the group consisting of an ATP assay, an MTT assay, an Alamar Blue assay, a Rhodarnine 123 assay, and Cytochrome C oxidase assay. Particularly preferable mitochondrial function assays are the ATP assay and the Cytochrome C oxidase assay. An alternatively useful mitochondrial function assay in the context of the present invention is an MTT assay.

In preferred embodiments, the fourth indicator of cell health discussed above is an indicator of energy balance assay selected from the group consisting of an ATP/ADP balance assay and oxygen consumption assay. Preferably, the energy balance assay is an ATP/ADP balance assay. In those CATS analyses that include one or more cell death assays, the cell death assay may be selected from the group consisting of cell number assay and an apoptosis assay such as a caspase activity assay, a $BCL_2$ assay, a BAX assay, or a DNA fragmentation assay. A preferred cell death assay for use in the CATS analyses is a CYQUANT cell number assay.

The CATS assays of the present invention may be advantageously employed to predict the in vivo cytotoxicity of any chemical compound, such as an agent for the treatment or prevention of infectious diseases, such as an antimicrobial agent; an agent for the treatment or prevention of cancers and other neoplastic diseases and conditions, such as an antitumor agent; an immunomodulator; a neurotransmitter; an agent for the treatment or prevention of a central nervous system (CNS) disease or disorder; an agent effective for the treatment or prevention of cardiovascular diseases; an agent for the treatment or prevention of pain; an agent for the treatment of metabolic diseases; and an anti-inflammatory agent.

In certain aspects of the invention, the CATS assays will employ cells in culture. In preferred embodiments, such a cell is of mammalian origin. For example, the cell may be a liver cell, a kidney cell, a brain cell, a fibroblast cell, a nerve cell, a skin cell, a lung cell, a spleen cell, an endometrial cell, a cardiac cell, a stomach cell, a breast cell, a stem cell, an embryonic stem cell, a hematopoietic cell; or a cell line derived from one of these cells. It is contemplated that the cell may be a primary cell or may be derived from a cell line. In specific embodiments, the cell is a liver cell. The liver cell is preferably a human liver cell or a rodent (e.g., rat) liver cell. In preferred aspects, the human liver cell may be selected from the group consisting of HepG2 (ATCC HB-8065), C3A (ATCC CRL-10741), DMS (ATCC CRL-2064), SNU-398 (ATCC CRL-2233), SNU-449 (ATCC CRL-2234), SNU-182 (ATCC CRL-2235), SNU-475 (ATCC CRL-2236), SNU-387 (ATCC CRL-2237), SNU-423 (ATCC CRL-2238), NCI-H630 (ATCC CRL-5833), NCI-H1755 (ATCC CRL-5892), PLC/PRF/5 (ATCC CRL-8024), Hep3B (HB-8064) and HTB-52 (ATCC HTB-52). In other preferred embodiments, the rat liver cell is selected from the group consisting of H4IIE (ATCC CRL-1548), MHI C1 (ATCC CCL-144), clone 9 (ATCC CRL-1439), BRL 3A (ATCC CRL-1442), H4TG (ATCC CRL-1578), H4IIEC3 (ATCC CRL-166), McA-RH7777 (ATCC CRL-1601) McA-RH8994 (ATCC CRL-1602), N1-S1 Fudr (ATCC CRl-1603) and N1-S1 (ATCC CRL-1604). Of course, these are merely preferred and exemplary cell lines and those of skill in the art will be well aware of other cells that may be used in the present invention.

Also contemplated by the present invention is a method of developing an agent for treating a disorder comprising assaying a plurality of compounds for a biological activity that correlates with a desired therapeutic effect; selecting one or more compounds with the desired biological activity; predicting in vivo cytotoxicity of the selected compound(s) according to a CATS analyses as described herein; selecting a compound with acceptably low levels of predicted cytotoxicity; and testing the compound for efficacy against the disease or disorder. The "biological activity" activity that is assayed may be any activity that a researcher or clinician would consider relevant in a drug development program. Exemplary biological activities include, for example, receptor binding, receptor blocking, or receptor stimulation activities; mitogenic or cell growth stimulation activities; cell growth inhibition activities; chemotactic or cell activation activities; assays for changes in cell morphology or other characteristics; assays for secreted factors (e.g., proteins, hormones, transmitters) from cells; and assays for up-regulation or down-regulation of transcription, translation, or intracellular protein trafficking or protein processing. The desired therapeutic effect will usually be the prevention or cure of a disease or disorder or slowing of its progression; and/or the amelioration of its symptoms or manifestations. Usually, there will exist a scientific theory or rationale as to why modulation of a particular biological activity would correlate with a desirable therapeutic or prophylactic effect. In a preferred embodiment, the testing step of compounds that demonstrate the desired biological activity and have acceptably low levels of predicted toxicity is performed in vivo. Testing in both animal models and clinical testing in humans is contemplated. In specific embodiments, the plurality of compounds to be assayed for biological activity are obtained from a chemical library of compounds. Alternatively, the plurality of compounds may be obtained through rational drug design. The method for developing agents is suitable for developing agents for the treatment for any medical disorder. For example, the method is useful for developing agents for the treatment of pain; Alzheimer's disease and other diseases or disorders of the central nervous system; metabolic disorders; cancers and other neoplastic diseases and disorders; diabetes; depression; immunodeficiency diseases; immunological diseases and disorders; autoimmune diseases and disorders; gastrointestinal disorders; cardiovascular diseases and disorders; inflammatory diseases; and infectious diseases such as a microbial, viral or fungal infections.

In a further variation, the method of developing an agent further includes at least one step of manufacturing a composition comprising the compound in a pharmaceutically acceptable diluent or carrier, such as water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, or cocoa butter, to name a few. For example, the method includes a step of manufacturing such a composition prior to the testing step, and the testing step involves administering the composition in vivo. In addition, or in the alternative, the method includes a step of manufacturing of the composition after the testing step, if the in vivo testing confirms that the agent is effective for treatment or prophylaxis of the disease or disorder with acceptable levels of toxicity. In addition to manufacturing, the method optionally further includes steps of packaging the composition in a container containing a label describing the composition and optionally describing its therapeutic indications. In addition, the method optionally further includes a step of administering the manufactured composition to a patient in need of therapeutic or prophylactic treatment for the disease or disorder.

In a closely related aspect, the method of developing the agent further includes a step of manufacturing a medicament for the treatment of the disease or disorder, the manufacturing involving formulating the compound in a pharmaceutically acceptable diluent or carrier.

In yet another aspect, the present invention provides a method of identifying a lead compound for drug development, comprising obtaining a library of compounds having a potential therapeutic activity; analyzing the library to eliminate compounds that are predicted to be cytotoxic, the analysis comprising predicting the cytotoxicity of the compounds according to the CATS analyses described herein; and selecting a compound from the library that has an acceptably low level of predicted cytotoxicity. In specific embodiments, the library of compounds is selected based on structural features of the compounds in the library.

In an additional aspect, the present invention provides a method of screening chemical compounds to select candidate therapeutic agents, comprising performing an in vitro activity assay to determine concentrations of chemical compounds required to achieve an activity ($C_{ther}$), wherein the activity correlates with a desired therapeutic effect in vivo; predicting cytotoxicity of the compounds according to the CATS analyses described in the present invention; and selecting as candidate therapeutic agents compounds having a $C_{ther}$ less than $C_{tox}$. The "activity" that is assayed may be any biochemical activity that a researcher or clinician would consider relevant in a drug development program, such as the exemplary biological activities described above. The therapeutic effect may be prevention, cure, or alleviation of symptoms associated with a disease or disorder as described herein, or other effect short of cure that improves the quality of life of a person suffering from a disease or disorder. In one further variation, the method further includes a step of manufacturing a composition comprising the compound in a pharmaceutically acceptable diluent or carrier. For example, the method includes a step of manufacturing such a composition with compounds selected as candidate therapeutic agents. In a closely related variation, the method further includes a step of manufacturing a medicament for the treatment of a disease or disorder, the manufacturing involving formulating the compound in a pharmaceutically acceptable diluent or carrier. In addition to manufacturing, the method optionally further includes steps of packaging the composition in a container containing a label describing the composition and optionally describing its therapeutic indications. In addition, the method optionally further includes a step of administering the manufactured composition to a patient in need of the compound's therapeutic effect.

In yet another aspect, the present invention provides a method of prioritizing candidate therapeutic agents for pharmaceutical research and development comprising performing an in vitro activity assay to determine concentrations of chemical compounds required to achieve an activity ($C_{ther}$), wherein the activity correlates with a desired therapeutic effect in vivo; predicting cytotoxicity of the compounds according to the CATS analyses as described in the present invention; determining the ratio of $C_{tox}:C_{ther}$ for each compound to provide an Estimated Therapeutic Index (ETI) for each compound; and prioritizing the compounds as candidate therapeutic agents from the ETIs wherein a higher ETI correlates with a higher priority for further development. The "activity" that is assayed may be any biochemical activity that a researcher or clinician would consider relevant in a drug development program, such as the exemplary biological activities described above. The therapeutic effect may be prevention, cure, or alleviation of symptoms associated with a disease or disorder as described herein, or other effect short of cure that improves the quality of life of a person suffering from a disease or disorder. In one further variation, the method further includes a step of manufacturing a composition comprising a compound that is highly prioritized on the basis of a high ETI score, the composition further comprising a pharmaceutically acceptable diluent or carrier. Optionally, the method further includes a step of administering the composition to a non-human animal or to a human for evaluation of in vivo toxicity/safety and/or efficacy.

Sometimes, it may be impossible or inconvenient to determine an ETI. In yet another aspect, the invention provides a method of prioritizing candidate therapeutic agents for pharmaceutical research and development comprising predicting cytotoxicity of the candidate therapeutic agents according to the CATS analyses as described in the present invention; and prioritizing the agents based on the exposure concentration of the agents that resulted in a half-maximal toxic response ($TC_{50}$) in one or more of the CATS assays employed. This approach may be especially valuable when the candidate therapeutic agents share a similar chemical structure and are expected to exhibit similar desirable biological activity.

In additional embodiments, the present invention describes methods of predicting the in vivo cytotoxicity of a chemical compound comprising culturing cells in culture medium that comprises a plurality of concentrations of a chemical compound; measuring a first indicator of cell health at four or more concentrations of said chemical compound; measuring a second indicator of cell health at four or more concentrations of said chemical compound; measuring a third indicator of cell health at four or more concentrations of said chemical compound; predicting a cytotoxic mechanism by which the chemical compound exerts cytotoxic effects from the measurements of steps said first, second and third indicators of cell health. In specific embodiments, the method further comprises predicting a toxic concentration ($C_{tox}$) of said chemical compound from the measurements obtained in the measuring steps.

Other embodiments provide kits that may be employed in conducting the various assays of the present invention.

Other aspects, features and advantages of the present invention will be apparent from the entirety of the application, including the drawings and detailed description, and all such features are intended as aspects of the invention.

Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

With respect to aspects of the invention that have been described as a set or genus, every individual member of the set or genus is intended, individually, as an aspect of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

Also, it should be understood that the detailed description presented below, while providing preferred embodiments of the invention, is intended to be illustrative only since changes and modification within the scope of the invention will be possible whilst still providing an embodiment that is within the spirit of the invention as a whole.

BRIEF DESCRIPTION OF THE DRAWINGS

The following drawings form part of this application and are included to further demonstrate certain aspects of the invention. The invention may be better understood by reference to one or more of these drawings in combination with the detailed description of the specific embodiments of the present invention.

FIG. 6A shows a dose response effect of ketoconazole on cell number, GST leakage, MTT and ATP assays to reveal a CATS toxicity profile of ketoconazole toxicity. FIG. 6B depicts the same data as FIG. 6A with line A indicating the $C_{tox}$ concentration as predicted by the present invention, line B indicating the actual toxicity in humans and line C indicating the actual toxicity in rats.

FIG. 9 is a graph which shows CATS analysis performed on an antifungal agent with high toxicity.

FIG. 10 is a graph which shows CATS analysis performed on an antifungal agent with low toxicity.

FIG. 11 is a graph which shows CATS analysis performed on an antifungal agent with a potentially unique mechanism of toxicity.

FIG. 13A shows the effects of compound A on general cell health following a 24 hour exposure. FIG. 13B shows the effects if compound B on general cell health following a 24 hour exposure.

FIG. 14A shows the effects of compound A on membrane integrity. FIG. 14B shows the effects of compound A on cell number. FIG. 14C shows the effects of compound A on markers of mitochondrial function. FIG. 14D shows the effects of compound A on cell health.

DETAILED DESCRIPTION OF THE INVENTION

Figure 1:
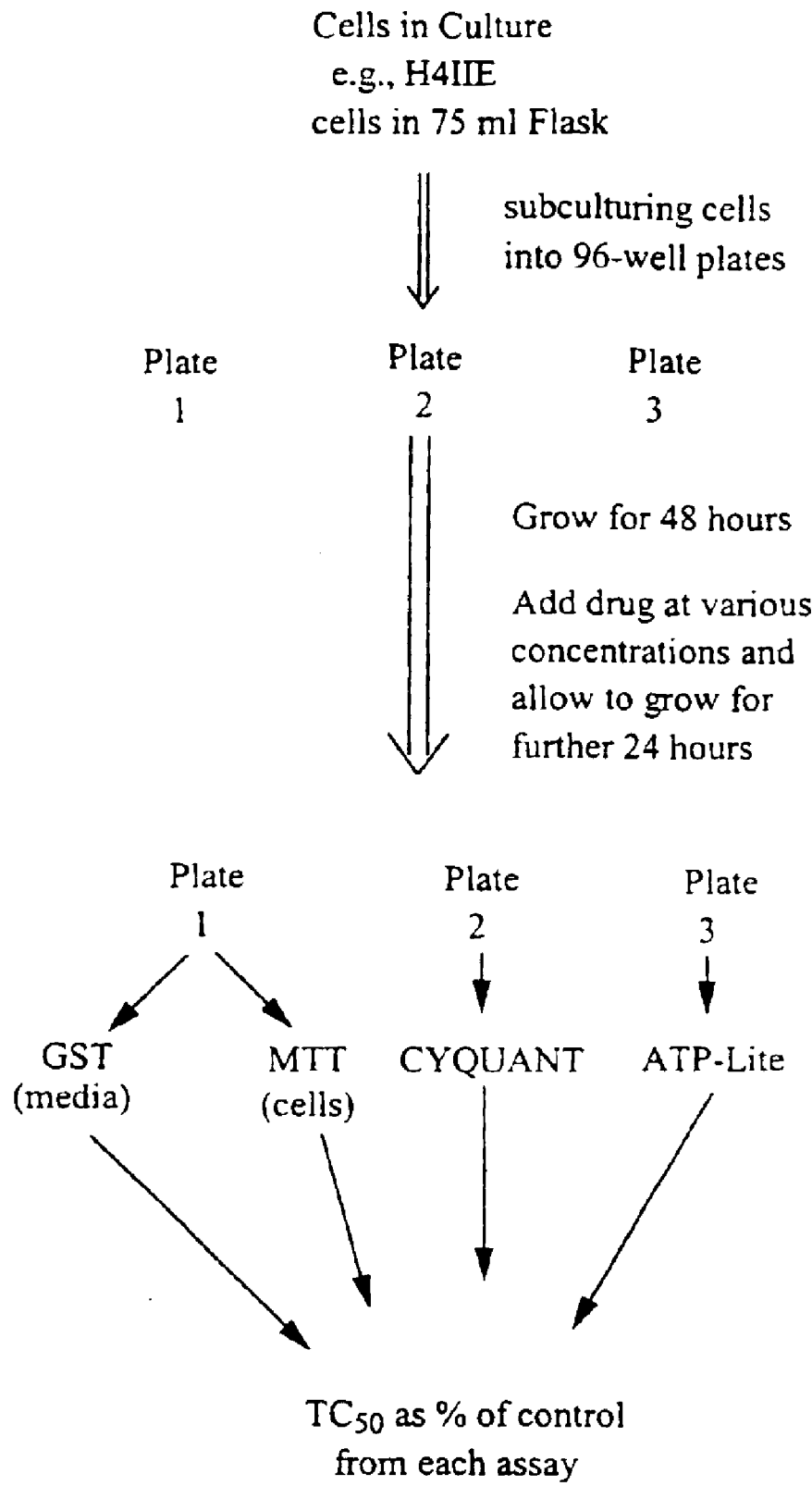
FIG. 1 is a schematic diagram which depicts the steps of one embodiment of a CATS assay.

Presently, it takes between three and five years to bring new potentially therapeutic compounds from the early discovery to preclinical development (in vivo animal testing). The toxicity data for such compounds is generally not available until the preclinical animal toxicity tests are performed. Numerous drugs reach this stage of development only to be discarded from further development due to toxic liability. Such failures represent a tremendous loss in company resources. Understandably, a technique that could predict the toxicity of these multitude of compounds that arrive at or near the initial synthesis stage of drug discovery would have an enormous impact on the efficiency with which new drugs are identified by eliminating, early in the drug discovery process, compounds that have an unfavorable toxicity profile. An immediate expected benefit of more powerful, early stage in vitro toxicity testing is the reduction of the number of these three to five year drug discovery cycles that result in failures, and thus reduce the average number of cycles required to develop successful new therapeutics. Related benefits include reduced costs for drug development and more rapid availability of new pharmaceuticals to the medical community. Reduced failure rates may lengthen the portion of a patent's term that valuable compounds enjoy commercial exploitation.

The present invention provides methods for prioritizing new chemical entities within a class for further development, identifying mechanisms of toxicity and for estimating in vivo toxicity early in the drug development and discovery process. As such, these methods can be used to prioritize large numbers of new compounds for further drug development. In addition, the methods greatly increase the probability that an identified agent will be successful in preclinical toxicity testing. The adaptability of these in vitro methods for high-throughput analysis makes them an economical and cost-effective addition to a drug discovery program.

In particular, the present invention provides a cluster analysis in which three or more different biochemical endpoints are evaluated in order to predict the in vivo toxicity concentration of a given compound, prioritize compounds based on relative toxicity, and identify mechanisms of toxicity. In preferred embodiments, these assays measure changes in specific biochemical processes, which are essential for normal cellular functions, following a 24-hour exposure to a broad range of concentrations of the compound.

The toxicity cluster analyses of the present invention allow the determination of appropriate information relating to changes occurring in specific cellular processes. This information in turn is used to obtain a more complete profile of cellular injury and/or cytotoxicity.

I. Cluster Analysis Toxicity Screening

In the present invention, cluster analysis toxicity screening is presented as a method of predicting the in vivo toxicity of a given compound. In particular aspects, these assays will involve culturing cells in culture medium that comprises a plurality of concentrations of the chemical compound; measuring a plurality of cell health indicators of the cell in response to culturing in at least three concentrations of the chemical compound and predicting $TC_{50}$ and a toxic concentration ($C_{tox}$) of the chemical compound from such measurements. The various embodiments involved in conducting such assays are described in further detail below.

Assay Format

In particularly preferred embodiments, the CATS technique will be used to prioritize and identify compounds that will be of a potential therapeutic value. The inventors have discovered that analyzing multiple endpoints yields significant information regarding the toxicity of a given compound.

In certain embodiments, the present invention concerns a method for identifying such compounds. It is contemplated that this screening technique will prove useful in the general prioritization and identification of compounds that will serve as lead therapeutic compounds for drug development. The invention is not limited to any specific class of compound and will be a useful addition to laboratory analyses directed at identifying new and useful compounds for the intervention of a variety of diseases and disorders including, but not limited to, Alzheimer's disease, other disorders and diseases of the central nervous system, metabolic disorders and diseases, cancers, diabetes, depression, immunodeficiency diseases and disorders, immunological diseases and disorders, autoimmune diseases and disorders, gastrointestinal diseases and disorders, cardiovascular diseases and disorders, inflammatory diseases and disorders, and infectious diseases, such as a microbial, viral or fungal infections.

In specific embodiments, the present invention is directed to a method for determining the in vivo cytotoxicity of a candidate substance by employing a method including generally:

a) culturing cells in culture medium that comprises a plurality of concentrations of said chemical compound;

b) measuring a first indicator of cell health at four or more concentrations of said chemical compound;

c) measuring a second indicator of cell health at four or more concentrations of said chemical compound;

d) measuring a third indicator of cell health at four or more concentrations of said chemical compound; and e) predicting a toxic concentration ($C_{tox}$) of said chemical compound from the measurements of steps (b), (c) and (d).

In certain aspects, the method may further involve predicting a $TC_{50}$ of said chemical compound from the measurements of steps (b), (c) and (d). For any particular assay, the $TC_{50}$ represents the concentration of a compound which causes fifty percent of a maximal toxic response in the assay. As described in greater detail below, when CATS is run under certain conditions, $TC_{50}$ can be selected as a predicted $C_{tox}$.

The foregoing method requires preparing cell cultures. Such a cell may be a primary cell in culture or it may be a cell line. The cells may be obtained from any mammalian source that is amenable to primary culture and/or adaptation into cell lines. In lieu of generating cell lines from animals, such cell lines may be obtained from, for example, American Type Culture Collection, (ATCC, Rockville, Md.), or any other Budapest treaty or other biological depository. The cells used in the assays may be from an animal source or may be recombinant cells tailored to express a particular characteristic of, for example, a particular disorder for which the drug development is being considered. Preferably, the cells are derived from tissue obtained from humans or other primates, rats, mice, rabbits, sheep and the like. Techniques employed in mammalian primary cell culture and cell line cultures are well known to those of skill in that art. Indeed, in the case of commercially available cell lines, such cell lines are generally sold accompanied by specific directions of growth, media and conditions that are preferred for that given cell line.

The present invention predicts the cytotoxicity of a given compound by measuring at least a first, second and third indicator of cell health in a given cell. The cell chosen for such an endeavor will depend on the putative site of in vivo toxicity to be determined. For example, the liver is a particularly prevalent site of in vivo drug toxicity. Thus, the use of liver cells (either primary or cell lines derived from liver cells) in the assays described herein is specifically contemplated. In preferred embodiments, the inventors have found that the H4IIE cell line (ATCC #CRL-1548) is an excellent candidate for predicting the cytotoxic effects of compounds on the general health of hepatic cells. In addition, because the H4IIE cell line is a proliferating cell population, the system will be useful in identifying compounds that adversely affect other proliferating cell types such as hematopoietic cells. Such cells can be used to identify chemotherapeutic agents that have extremely low hepatotoxicity but high toxicity to proliferating cells. (See Example 5).

While the H4IIE cell line is described herein as a preferred cell line, it should be understood that any mammalian primary hepatic cell or hepatic cell line will be useful in the present invention. In certain preferred embodiments, the cell is a rat hepatic cell line. In addition to H4IIE, other preferred rat cell lines contemplated for use in the present invention include, but are not limited to MH1C1 (ATCC CCL144), clone 9 (ATCC CRL-1439), BRL 3A (ATCC CRL-1442), H4TG (ATCC CRL-1578), H4IIEC3 (ATCC CRL-166), McA-RH7777 (ATCC CRL-1601) McA-RH8994 (ATCC CRL-1602), N1-S1 Fudr (ATCC CRL-1603) and N1-S1 (ATCC CRL-1604).

In other preferred embodiments, the cell is a human liver cell. A preferred human hepatic cell line for use in the methods described by the present invention is HepG2 (ATCC HB-8065). Additionally, other exemplary human hepatic cell lines that may be useful in the present invention include but are not limited to C3A (ATCC CRL-10741), DMS (ATCC CRL-2064), SNU-398 (ATCC CRL-2233), SNU-449 (ATCC CRL-2234), SNU-182 (ATCC CRL-2235), SNU-475 (ATCC CRL2236), SNU-387 (ATCC CRL-2237), SNU-423 (ATCC CRL-2238), NCI-H630 (ATCC CRL-5833), NCI-H1755 (ATCC CRL-5892), PLC/PRF/5 (ATCC CRL8024), Hep3B (HB-8064) and HTB-52 (ATCC HTB-52).

While the above cells will be useful indicators of hepatic cell toxicity, the present invention may be employed to determine, monitor or otherwise predict cytotoxicity in a variety of tissue types. It should be understood that the in vivo sites of cellular toxicity that those of skill in the art will want to monitor will include the in vivo sites of action of the particular test compound as well as sites remote from the site of action of the test compound. Therefore, cell lines that may be used in assays will include cell lines derived from other common sites of in vivo cytotoxicity such as the kidney, heart and pancreas. While these tissues, along with the liver, may be the primary tissues that one would select to monitor cytotoxicity, it should be understood that the assays of the present invention may be employed to predict the cytotoxic effects of a test compound on cells derived from brain, nerve, skin, lung, spleen, endometrial, stomach and breast tissue, as well as stem cells and hematopoietic cells. Use of hematopoietic cells or "stem" cells or cell lines derived therefrom in cytotoxicity assays is particularly contemplated.

In particular embodiments, the cells are seeded in multi-well (e.g. 96-well) plates and allowed to reach log phase growth. In H4IIE cells, this growth period is approximately 48 hours. Preferred media and cell culture conditions for this cell-line are detailed in the Examples.

Once the cell cultures are thus established, various concentrations of the compound being tested are added to the media and the cells are allowed to grow exposed to the various concentrations for 24 hours. While the 24 hour exposure period is preferred, it should be noted that this is merely an exemplary time of exposure and testing the specific compounds for longer or shorter periods of time is contemplated to be within the scope of the invention. As such it is contemplated that the cells may be exposed for 6, 12, 24, 36, 48 or more hours. Increased culture times may sometimes reveal additional cytotoxicity information, at the cost of slowing down the screening process.

Furthermore, the cells may be exposed to the test compound at any given phase in the growth cycle. For example, in some embodiments, it may be desirable to contact the cells with the compound at the same time as a new cell culture is initiated. Alternatively, it may be preferable to add the compound when the cells have reached confluent growth or are in log growth phase. Determining the particular growth phase cells are in is achieved through methods well known to those of skill in the art.

The varying concentrations of the given test compound are selected with the goal of including some concentrations at which no toxic effect is observed and also at least two or more higher concentrations at which a toxic effect is observed. A further consideration is to run the assays at concentrations of a compound that can be achieved in vivo. For example, assaying several concentrations within the range from 0 micromolar to about 300 micromolar is commonly useful to achieve these goals. It will be possible or even desirable to conduct certain of these assays at concentrations higher than 300 micromolar, such as, for example, 350 micromolar, 400 micromolar, 450 micromolar, 500 micromolar, 600 micromolar, 700 micromolar, 800 micromolar, 900 micromolar, or even at millimolar concentrations. The estimated therapeutically effective concentration of a compound provides initial guidance as to upper ranges of concentrations to test. Additionally, as explained in greater detail below, CATS analysis preferably includes assaying a range of concentrations that includes at least two concentrations at which cytotoxicity is observable in an assay. It has been found that assaying a range of concentrations as high as 300 micromolar often satisfies this criterion.

In an exemplary set of assays, the test compound concentration range under which the CATS is conducted comprises dosing solutions which yield final growth media concentration of 0.05 micromolar, 0.1 micromolar, 1.0 micromolar, 5.0 micromolar, 10.0 micromolar, 20.0 micromolar, 50.0 micromolar, 100 micromolar, and 300 micromolar of the compound in culture media. As mentioned, these are exemplary ranges and it is envisioned that any given assay will be run in at least four different concentrations, more preferably the concentration dosing will comprise, for example, 4, 5, 6, 7, 8, 9, 10, 11, 12, 13, 14, 15 or more concentrations of the compound being tested. Such concentrations may yield, for example, a media concentration of 0.05 micromolar, 0.1 micromolar, 0.5 micromolar, 1.0 micromolar, 2.0 micromolar, 3.0 micromolar, 4.0 micromolar, 5.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 55.0 micromolar, 60.0 micromolar, 65.0 micromolar, 70.0 micromolar, 75.0 micromolar, 80.0 micromolar, 85.0 micromolar, 90.0 micromolar, 95.0 micromolar, 80.0 micromolar, 110.0 micromolar, 120.0 micromolar, 130.0 micromolar, 140.0 micromolar, 150.0 micromolar, 160.0 micromolar, 170.0 micromolar, 180.0 micromolar, 190.0 micromolar, 200.0 micromolar, 210.0 micromolar, 220.0 micromolar, 230.0 micromolar, 240.0 micromolar, 250.0 micromolar, 260.0 micromolar, 270.0 micromolar, 280.0 micromolar, 290.0 micromolar, and 300 micromolar in culture media. It will be apparent that a cost-benefit balancing exists in which the testing of more concentrations over the desired range provides additional information, but at additional cost, due to the increased number of cell cultures, assay reagents, and time required. In a highly preferred embodiment, ten different concentrations over the range of 0 micromolar to 300 micromolar are screened.

Typically, the various assays described in the present specification may employ cells seeded in 96 well plates or even 384 cell plates. The cells are then exposed to the test compounds over a concentration range, for example, 0–300 micromolar. The cells are incubated in these concentrations for a given period of, for example, 24 hours. Subsequent to the incubation, the assays of the cluster are performed for each test compound. It is preferable that all the assays are performed at the same time such that a complete set of data are generated under similar conditions of culture, time and handling. However, it may be that the assays are performed in batches within a few days of each other.

In specific embodiments, the indicators of cell health and viability include but are not limited to cellular replication, mitochondrial function, energy balance, membrane integrity and cell mortality.

The CATS assays are quite straightforward to set up and perform. For example, one admixes a candidate substance with a suitable cell, under conditions which allow the monitoring of one or more of the assays. FIG. 1 shows a scheme in which the rat hepatoma cells are used as a model system and grown into 96-well assay format. This multiwell format allows one to conduct various permutations of the individual assays from the cluster assays on a single assay plate.

The compounds to be tested may include fragments or parts of naturally-occurring compounds or may be derived from previously known compounds through a rational drug design scheme. It is proposed that compounds isolated from natural sources, such as animals, bacteria, fungi, plant sources, including leaves and bark, and marine samples may be assayed as candidates for the presence of potentially useful pharmaceutical compounds. Alternatively, pharmaceutical compounds to be screened for toxicity could also be synthesized (i.e., man-made compounds).

The types of compounds being monitored may be anti-viral compounds, antibiotics, anti-inflammatory compounds, antidepressants, analgesics, antihistamines, diuretic, antihypertensive compounds, antiarrythmia drugs, chemotherapeutic compounds for the treatment of cancer, antimicrobial compounds, among others.

Regardless of the source or type of the compound to be tested for cytotoxicity, it may be necessary to monitor the biological activity of the compounds to provide an indication of the therapeutic efficacy of a particular compound or group of compounds. Of course, such assays will depend on the particular therapeutic indication being tested. Exemplary indications include efficacy against Alzheimer's disease, cancer, diabetes, depression, immunodeficiency, autoimmune disease, gastrointestinal disorder, cardiovascular disease, inflammatory disease and the like.

Cluster Analyses Assays

The use of multiple assays to develop a toxicity profile for new drugs proves to be a very powerful tool for accurately assessing the effects of a compound in a living system.

Selective assays used in the clusters of the present invention provide key information pertaining to the toxicity profile of a given compound. The assays are preferably performed such that information regarding the various parameters is obtained at the same time during the drug development phase of drug discovery as opposed to performing the assays at different times during the drug development scheme. Preferably, the assays are performed in a batch all at the same time. In other preferred aspects, it may be useful to perform the assays on cell cultures all generated at the same time from an initial cell line.

Modules may be designed in which a cluster of assays address a specific concern. Thus, in order to monitor the effect of a specific compound on the general health of a cell, monitoring membrane integrity, mitogenesis, mitochondrial function and energy balance will be particularly useful. The specific assay employed for any of these endpoints is not considered to be limiting. Thus, any assay that provides an indication of membrane integrity may be combined with any assay that is predictive of mitogenesis (cell replication) along with any assay that is an indicator of mitochondrial function and energy balance.

In addition to a module for determining the general cell health, other modules of interest would include those that are directed to determining for example, oxidative stress, cell cycle parameters, acute inflammatory response, apoptosis and endocrine responses.

In a module that determines oxidative stress, exemplary assays to be employed in the cluster my involve monitoring endpoints that include but are not limited to glutathione/ glutathione disulfide (GSH/GSSG), dichlorofluoroscindiacetate (DCFDA), lipid peroxidation, 8-isoprostane, 8-oxy guanine (8-oxy G) DNA adducts, thiobarbituric acid (TBARS), and malondialdehyde (MDA).

Modules designed to monitor cell cycle may include determining the effect on the presence or level of any given cell cycle indicator including but not limited to p53, p21, TGFβ, CDK1, PCNA, telomerase, nitric oxide, and inducible nitric oxide synthase (iNOS). Again any particular assay may be employed to determine the level or amount of any given cell cycle indicator.

As stated above the specific assay to monitor any of the given parameters is not considered crucial so long as that assay is considered by those of skill in the art to provide an appropriate indication of the particular biochemical or molecular biological endpoint to be determined, such as information about mitochondrial function, energy balance, membrane integrity, cell replication, and the like. The following sections provides exemplary assays that may be used in the context of the present invention. This is not intended to be an exhaustive treatise on the description of these assays but rather a guidance as to the type of assays that are available to those of skill in the art.

Compounds that produce direct effects on the cells typically alter mitochondrial function, by either up- or down regulating oxidative respiration. This means that cellular energy in the form of ATP may be altered. Mitochondrial function can be used as an indicator of cytotoxicity and cell proliferation. Healthy mitochondria catalyze the reduction of 3-(4,5-dimethylthiazol-2-yl)-2,5-diphenyltetrazolium bromide (MTT) to a blue or purple formazan compound. The relatively insoluble formazan blue is extracted into isopropanol and the absorbance of the extract measured. A high absorbance value indicates viable cells and functional mitochondria. Conversely, a decrease in the intensity of color suggests either a loss of cells, or direct toxic effects on the mitochondria. The MTT assay is well known to those of skill in the art and has been described in for example, the MTT mitochondrial dye assay is described in Mosmann, *J Immunol. Methods* 65, 55–63, 1983 and in Denizot et al., *J Immunol. Methods.* 89, 271–277, 1986. A similar assay that monitors XTT mitochondrial dye is described by Roehm et al., *J. Immunol. Methods,* 142, 257–265, 1991. In addition, those of skill in the art also may determine mitochondrial function by performing for example an Alamar Blue assay [Goegan et al., *Toxicol. In Vitro* 9, 257–266. 1995], a Rhodamine 123 assay, or a cytochrome C oxidase assay.

ATP provides the primary energy source for many cellular processes and is required to sustain cell and tissue viability. Intracellular levels of ATP decrease rapidly during necrosis or apoptosis. Therefore, changes in the cellular concentration of ATP can be used as a general indicator of cell health, when normalized on a per cell basis ATP can provide information on the energy status of the cell and may provide a marker to assess early changes in glycolytic or mitochondrial function. Assays that allow a determination of ADP/ ATP energy balance are well known in the art. (Kangas et al., *Med Biol,* 62, 338–343, 1984).

Measurements of A-GST leakage from cultured cells into the media can be used to assess membrane integrity. This assay is specific for the alpha form of GST that exists at high concentrations in the cytosol of hepatocytes. An ELISA kit purchased from Biotrin Inc. was used to measure GST. GST leakage assays, have been described in the literature, for example, Redick et al., *J Biol. Chem.* 257, 15200–15203. Oberley et al., *Toxicol. Appl. Pharmacol.* 131, 94–107, 1995; Feinfeld, *J Clin Chem Clin Biochem.* 24, 529–532, 1986.

Other assays for determining membrane integrity include, but are not limited to, assays that determine lactate dehydrogenase activity, aspartyl aminotransferase, alanine aminotransferase, isocitrate dehydrogenase, sorbitol dehydrogenase, glutamate dehydrogenase, ornithine carbamyl transferase, γ-glutamyl transferase, and alkaline phosphatase.

The ability of cells to divide requires coordinated signaling between a vast array of intracellular receptors. Cell replication or "mitogenesis" requires the cells to be functioning at optimum. A change in the ability to replicate is therefore an indication of stress or abnormal function. An exemplary assay that will allow the determination of cell replication is the CYQUANT® assay system described in *In vitro toxicol* 1990, 3, 219; *Anal. Biochem.* 1993, 213, 426. Additional assays that may be used to provide an indication of the mitogenesis may include but are not limited to monitoring $^3$H-thymidine incorporation; a BrdU incorporation assay. In addition, mitogenesis may be monitored by determining the function, presence or absence of a component that controls cell cycle. Exemplary components will be well known to those of skill in the art and include but are not limited to p53, p21, TGFβ, CDK1, PCNA and the like.

Certain of the assays performed as part of the CATS analysis will involve measuring components of the media whereas others will involve measuring cell number or parameters from the cells or cell lysates. The CATS analysis advantageously involves selecting some assays that can use media and others that can use cells from a single well.

Predicting In Vivo Toxicity of a Compound from In Vitro Analyses

Once all data for a given cluster of assays are received, the data are analyzed to obtain a detailed profile of the compound's toxicity. For example, most conveniently, the data are collated over a dose response range on a single graph. In such an embodiment, the measurement evaluated for each parameter (i.e., each indicator of cell health) at any given concentration is plotted as a percentage of a control measurement obtained in the absence of the compound. However, it should be noted that the data need not be plotted on a single graph, so long as all the parameters are analyzed collectively to yield detailed information of the effects of the concentration of the compound on the different parameters to yield an overall toxicity profile. As set forth below, this overall toxicity profile will facilitate a determination of a plasma concentration $C_{tox}$ that is predicted to be toxic in vivo. $C_{tox}$ represents an estimate of the sustained plasma concentration in vivo that would result in toxicity, such as hepatotoxicity or hematopoietic toxicity.

A fundamental premise in the field of toxicology is that all compounds are poisons, and that it is the dose of the compound that determines a beneficial/therapeutic effect versus a toxic effect. Dose is affected by time of exposure, dosing regimens, pharmacokinetic parameters such as absorption, metabolism and elimination, by difference between species being treated, and by route of administration. All these factors influence the plasma concentration of a drug and its duration of exposure. Thus, in principle, in vitro screens need only account for metabolism and time of exposure. In theory, an increased exposure time should shift the dose response curve to the left (e.g., $TC_{50}$ is lower or the compound appears more toxic over longer exposure times). These factors all have been considered in the selection of $C_{tox}$ in the CATS assay.

For example, in vitro time course experiments utilizing the H4IIE cells were conducted to evaluate the change in the dose-response curves for chloramphenical and ketoconazole over a 72 hour exposure period. The data indicated that the largest shift in $TC_{50}$ values occurred between 24 and 48 hours and that extended exposures (72 hours) had little or no effect on the toxicity profile. From these data it was determined that the NOEL of the 24-hour exposure correlated well with in vivo toxicity and provided acceptable estimates of the plasma concentration in vivo that would result in toxicity. When compared to in vivo animal studies, the 24-hour $TC_{50}$ concentration for the most sensitive toxicity exceeded the concentration at which toxicity occurred. However, the NOEL of the 24 hour period also correlated with the 72-hour $TC_{50}$ concentration for the more sensitive assays, and thus the 72-hour $TC_{50}$ concentration also provided acceptable estimates of the plasma concentration in vivo that would result in toxicity.

Studies such as these indicate that a preferred concentration for setting $C_{tox}$ is the highest concentration at which there is no observed effect on any of the indicators being measured in the cluster analysis, especially a 24-hour cluster analysis. The $TC_{50}$ concentration in the most sensitive of toxicity assays in a 72 hour cluster analysis has been observed to correlate with the 24 hour NOEL/$C_{tox}$, and thus represents another datapoint in the CATS analysis that works as an estimate of the sustained plasma concentration in vivo that would result in toxicity. It will be apparent that 24 hour assays are more time-effective, and consequently, the 24 hour NOEL/$C_{tox}$ represents a preferred data point to select as $C_{tox}$ in a CATS assay. It will also be apparent that, with further time studies, it may be possible to select an equally suitable $C_{tox}$ at other CATS assay time points (e.g., between 24 and 72 hours, or less than 24 hours).

Figure 12:
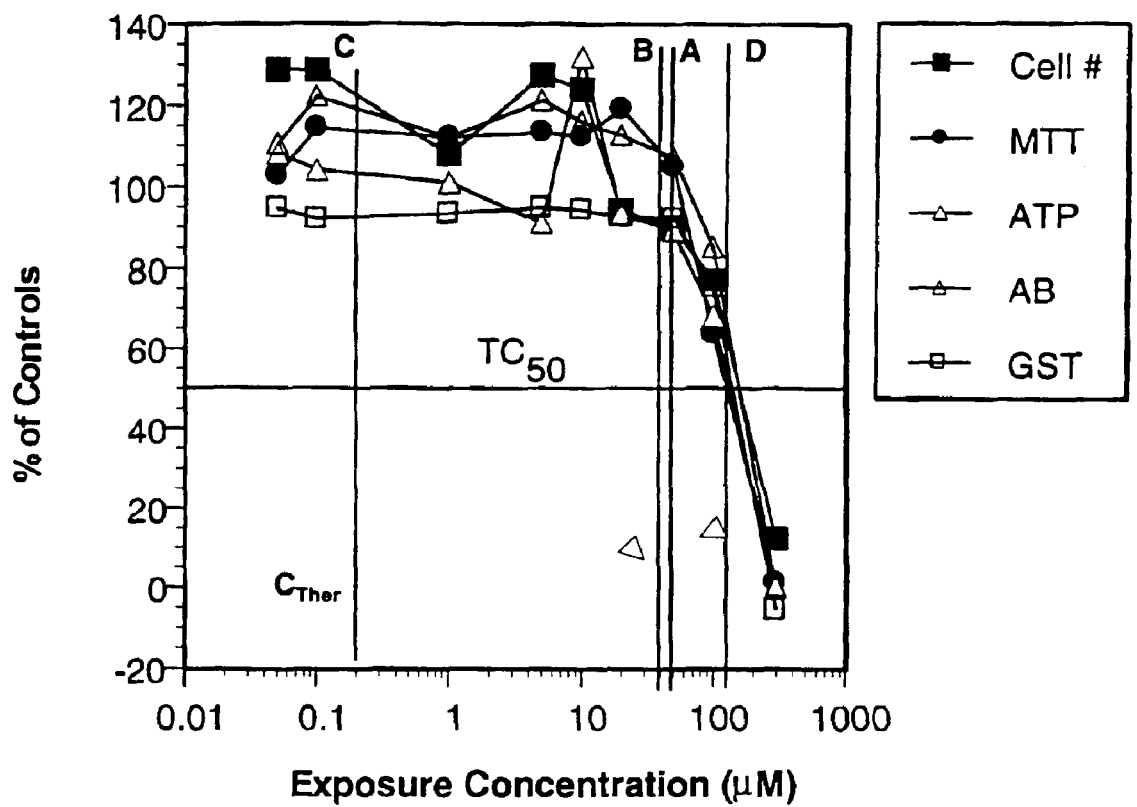
FIG. 12 is a graph which shows the in vitro cluster analysis (CATS) prediction of in vivo toxicity ($C_{tox}$).

In preferred aspect, the data derived from performing a cluster analysis is presented in a single graphic plot of the relative effect of the compound (relative to control) on any given parameter being measured as a function of concentration of the compound. The $C_{tox}$ is the estimated concentration at which the compound would cause a toxic effect in vivo. To find $C_{tox}$ the highest concentration on the 100% line that had no effect in the in vitro toxicity cluster assay is determined as the putative no effect level NOEL (FIG. 12). The identification of this NOEL value is most reliable when it is followed by at least two higher concentrations that produce observable dose-related toxic effects (to distinguish random experimental fluctuations from first observed toxic effects). A vertical line is then drawn beginning at the NOEL point and ending as it intersects the X-axis (line A in FIG. 12). The concentration value on the X-axis intersected by this line represents the predicted plasma concentration that would cause toxicity in vivo ($C_{tox}$). The therapeutic concentration or dose is the required plasma concentration that produces a desired therapeutic effect without a concomitant cytotoxic effect. For drug candidates, it is preferred that the effective or therapeutic dose ($C_{ther}$) is sufficiently separated from the toxic dose ($C_{tox}$) to permit effective treatment with minimum risk of toxic closing. In preferred embodiments, the $C_{ther}$ is at least 10-fold or less than $C_{tox}$. In the example shown in FIG. 12 the actual plasma concentration, in vivo, where hepatic toxicity was first observed is indicated by the vertical line (B). The predicted (A) and the actual (B) values are within 20% of each other. The plasma concentration that was observed to produce a desired therapeutic effect is indicated by line (C). The concentration range between lines (C) and (B) represent a "therapeutic window" in which the drug is effective without exerting toxicity. Line (D) in FIG. 12 represents the $TC_{50}$ concentration, i.e., the concentrations at which the MTT, GST, and ATP assays exhibited 50% maximum toxic effect in this 24 hour CATS analysis. The $TC_{50}$ of the Alamar Blue and cell number assays is greater than that seen from the MTT, GST, and ATP assays. At the 24 hour time point, NOEL provides a better prediction than $TC_{50}$ of the toxic concentration of the drug.

In preferred embodiments, the predicting comprises performing dose response analyses of measurements from at least three separate assays that are employed in the cluster analysis. For example, in the cell health cluster, such predicting will involve monitoring the dose response effect of the compound on a first health indicator which monitors cellular replication, a second cell health indicator which monitors mitochondrial function, and a third cell health indicator which monitors membrane integrity. Of course, it is understood that fourth, fifth, sixth or more cell health indicator also may be employed. From these dose response analyses, the highest concentration of the chemical compound at which a measurable toxic effect of the chemical compound is not observable, i.e. NOEL, is determined and the $C_{tox}$ is identified as the concentration that correlates to the NOEL. In choosing the concentrations of the compound for analysis, one of skill in the art should devise a dose response regimen which is selected to provide an indication of cell health at concentrations of at least two concentration values higher than the $C_{tox}$ concentration.

In the specific embodiments, the results of the analyses are depicted on a single graph on which the values are presented relative to control. The term "relative to control" means that the measurements in the presence of a given concentration of the compound are compared to a similar assay performed in the absence of the compound. The measurement in the absence of the compound is presented as the 100% measurement in FIG. 12. The effect of the compound is thus determined as a raw figure which is then adjusted relative to that measurement that is determined in the absence of the compound.

In certain instances, there may be enough biological activity information generated for a compound or series of compounds from efficacy/activity experiments to predict a plasma concentration in humans that will be required to see a therapeutic effect. Even where such a prediction is premature, there may at least be some activity data indicating concentration of a compound or series of compounds needed to achieve a biological effect that correlates with a desired therapeutic activity. In such instances, it becomes possible to use the in vitro data from CATS analysis to estimate a therapeutic index (TI). TI for a drug is calculated by dividing the toxic concentration (conventionally a $TC_{50}$ value) by the beneficial therapeutic concentration. Thus, the larger the TI number, the safer the drug. For example, for a compound which has a $TC_{50}$ value greater than 100 micromolar, an estimated $C_{tox}$ value of 50 micromolar and an estimated therapeutic concentration of 0.2 micromolar, a TI of 500 is obtained. If the estimated $C_{tox}$ is used as the toxic concentration, then a TI of 250 is obtained. This would represent a safe drug at least in terms of liver toxicity. A TI that is at least 10 is preferred, and a TI of 100 is particularly preferred. Of course, values higher than 100 will be indicative of the drug being especially safe and would be most preferred.

Thus, in one embodiment of the invention useful for prioritizing candidate therapeutic agents, one performs an in vitro activity assay to determine concentrations of chemical compounds required to achieve an activity ($C_{ther}$), wherein the activity correlates with a desired therapeutic effect in vivo; predicts cytotoxicity of the compounds according to CATS assay procedures described herein; determines the ratio of $C_{tox}$:$C_{ther}$ for each compound to provide an Estimated Therapeutic Index (ETI) for each compound; and prioritizes the compounds as candidate therapeutic agents from the ETIs, wherein a higher ETI correlates with a higher priority for further development. The use of an estimated $TC_{50}$ from the CATS assays also would be suitable for generating ETIs and prioritizing compounds, especially where one is working with a family of structurally related compounds, and the $TC_{50}$ is from the same particular assay in the CATS battery of assays. (A primary piece of data often used to compare relative toxicity of compounds is the concentration of drug that produces a half maximal effect in any given assay. This value is referred to as the toxic concentration that produces a 50% response or $TC_{50}$.)

II. Use of Toxicity Cluster Assays to Identify Potential Non-Toxic New Therapeutics In preferred embodiments, the assays of the present invention may be used as part of a drug discovery program to identify a putative therapeutic compound with limited toxicity. Drug discovery begins with the identification of a range of candidate substances that show promise in a targeted therapeutic area. This first step can result in several hundred "hits". The discovery team is then faced with the question of which compounds to run in subsequent screens. CATS analysis at this stage allows teams to prioritize the compounds based on estimated toxicity or estimated relative toxicity values. The top compounds are put through a range of additional screens for efficacy and specificity. The idea is to identify the core structure or template that shows the most promise for future drug development efforts. Once the template is selected, additional chemistry and structure activity analyses are performed to increase the potency of the compound. This process yields the lead compounds. A CATS screen at this stage of the process may be performed to provide toxicity data on these potential lead compounds. The top lead compounds are selected to enter preclinical animal testing. At the animal testing stage, 30% of all drug candidates fail due to unanticipated toxicity. Incorporation of CATS screening early in the discovery process should greatly reduce the number of compounds that fail during this late stage.

The CATS technique described in the present invention may be employed at any stage in the drug discovery program but is especially valuable early in the discovery process. The information obtained from the cluster analysis provides the chemists with the appropriate information to design out toxicity, while maximizing potency and efficacy in the new templates. In addition, data obtained from the toxicity cluster analysis can identify subcellular targets of the compounds that generate the toxicity. Using these methods, the putative therapeutic compounds can be ranked or prioritized based on their relative toxicities and relative toxicity compared to known drugs in the same therapeutic and chemical class. For example, the antifungal ketoconazole could be used as a reference compound for new antifungals of the azole class.

High throughput assays for screening numerous compounds for toxicity are specifically contemplated. In certain embodiments, the high throughput screens may be automated. In high throughput screening assays, groups of compounds are exposed to a biological target. These groups may be assembled from collections of compounds previously individually prepared and since stored in a compound bank, the assembly being random or guided by the use of similarity programs from which similar structures are formed.

In addition, there has also been a rapid growth in the deliberate preparation and use of libraries and/or arrays of compounds. Each library contains a large number of compounds which are screened against a biological target such as an enzyme or a receptor. When a biological hit is found, the compound responsible for the hit is identified. Such a compound, or lead, generally exhibits relatively weak activity in the screen but forms the basis for the conduct of a more traditional medicinal chemistry program to enhance activity. The libraries may be prepared using the rapidly developing techniques of combinatorial chemistry or by parallel synthesis (DeWitt el al, *Proc Natl Acad Sci*, 90, 6909, 1993; Jung et al, *Angew Chem Int Ed Engl*, 31:367–83, 1992; Pavia etal., *Bioorg Med Chem Lett*, 3:387–96, 1993).

Alternatively, the compounds to be screened may be from a library based upon a common template or core structure [see for instance Eliman and Bunin, *J Amer Chem Soc*, 114:10997, 1992 (benzodiazepine template), WO 95/32184 (oxazolone and aminidine template), WO 95/30642 (dihydrobenzopyran template) and WO 95/35278 (pyrrolidine template)]. The template will have a number of functional sites, for instance three, each of which can be reacted, in a step-wise fashion, with a number of different reagents, for instance five, to introduce 5×5×5 different combinations of substituents, giving a library containing 125 components. The library will normally contain all or substantially all possible permutations of the substituents. The template may be a 'biased' template, for instance incorporating a known pharmacophore such as a benzodiazepine ring or an 'unbiased' template, the choice of which is influenced more by chemical than biological considerations.

Thus, the present invention may be used to identify lead compounds for drug discovery. In addition to the library screening discussed above, such lead compounds may be generated by random cross screening of single synthetic compounds made individually in the laboratory or by screening extracts obtained from natural product sources such as microbial metabolites, marine sponges and plants.

In another alternative, the compounds may be generated through rational drug design based on the structure of known biologically active compounds and/or their sites of biological action. This has now been complemented by the powerful techniques of computer-assisted drug design. The goal of rational drug design is to produce structural analogs of biologically active molecules of interest. Such technologies will yield potentially thousands of compounds for a particular indication that may be screened for cytotoxicity using the present invention.

III. Kits

In certain aspects of the present invention, all the necessary components for conducting the CATS assays may be packaged into a kit. Specifically, the present invention provides a kit for use in a cytotoxicity assay, the kit comprising a packaged set of reagents for conducting a first cytotoxicity assay selected from the group consisting of a cycle evaluation assay, mitochondrial function assay, energy balance assay and cell death assay; a second cytotoxicity assay selected from the group consisting of a cycle evaluation assay, mitochondrial function assay, energy balance assay and cell death assay; and a third cytotoxicity assay selected from the group consisting of a cycle evaluation assay, mitochondrial function assay, energy balance assay and cell death assay; wherein said first, second and third cytotoxicity assays are distinct from each other. The kits also may comprise the reagents for conducting a fourth or fifth cytotoxicity assay selected from selected from the group consisting of a cycle evaluation assay, mitochondrial function assay, energy balance assay and cell death assay. In addition to the reagents, the kit preferably also includes instructions packaged with the reagents for performing one or more variations of the CATS assay of the invention using the reagents. The instructions may be fixed in any tangible medium, such as printed paper, or a computer-readable magnetic or optical medium, or instructions to reference a remote computer data source such as a world wide web page accessible via the internet.

While the above embodiments contemplate kits in which there is one assay performed from each of the classes of cycle evaluation, mitochondrial function, energy balance and cell death assays it is contemplated that the kits and the methods may involve conducting more than one of any type of the assay. As such in addition to the kits comprising the reagents for a first, second, third, fourth and fifth assay, it is contemplated that the kits also may comprise the reagents for conducting a second assay from each of the classes. Therefore, it is contemplated that the kits also may comprise the reagents for conducting a plurality of distinct cell cycle evaluation assays; the reagents for conducting a plurality of distinct mitochondrial function assays; the reagents for conducting a plurality of distinct energy balance assays and the reagents for conducting a plurality of distinct cell death assays.

IV. Examples

The following examples present preferred embodiments of the invention. Those of skill in the art will understand that the techniques described in these examples represent techniques described by the inventors to function well in the practice of the invention, and as such constitute preferred modes for the practice thereof. Those of skill in the art will appreciate that many changes can be made in the specific methods which are disclosed without departing from the spirit and scope of the invention.

EXAMPLE 1

Materials and Methods

The present Example describes exemplary materials and methods that may be employed in certain aspects of the present invention and were used to generate the results described in the subsequent Examples.

Preparation of Stock dosing solutions

The test compounds were received pre-weighed into glass vials. The preparation of 20 millimolar stock solutions was accomplished by adding a sufficient amount of dimethylsulfoxide (DMSO) directly into the vials. These stocks were used to prepare 200 micromolar stock solutions in DMSO. Both the 20 millimolar and 200 micromolar, stocks were used to prepare dosing solutions of 0.05, 0.1, 1.0, 5.0, 10.0, 20.0, 50.0, 100, and 300 micromolar in culture media with a final DMSO concentration of 0.5%. The stocks and dosing solutions were prepared on the day prior to dosing. The solutions were wrapped in foil and stored at 4° C. until the next morning.

Test and Control Articles

Negative controls of media plus DMSO (0.5%) were included with and without cells. A digitonin (1 mM) treated group was included as a positive control for complete cell death.

Cell Line and Growth Media

Rat hepatoma derived H4IIE cells were used as the test system. The cells were obtained from ATCC (# CRL-1548) and subcultured in the laboratory. The culture medium used for these cells was Eagle's Minimum Essential Medium (MEM) with 10% Fetal Bovine Serum (FBS) and 10% calf serum. Certified FBS and calf serum were from Gibco Life Technologies.

Treatment and Experimental Design 96-well plates were seeded with 10,000 cells/plate in 200 microliters of media 48 hour prior to dosing. On the morning of the third day after seeding, the test compounds were added to the plates in a 200 microliter volume of medium (DMSO=0.5%). The 300 micromolar treatment had a final DMSO concentration of 1.5%.

During method development experiments the effect of DMSO on cell proliferation, MTT, and GST were evaluated at DMSO concentrations ranging from 0.01 to 4%. These studies showed no effects on any of the endpoints tested at concentrations of DMSO below 2%. In addition, the ability of DMSO to enhance cell uptake and hence toxicity of a compound was also evaluated using ketoconazole and amphotericin. No significant differences in toxicity were detected when a broad range of ketoconazole and amphotericin concentrations were tested at final DMSO concentrations of (0%, 0.5% and 1.0%).

Glutathione S-transferase (GST) leakage Assay:

On the morning after dosing the cells (approximately 24 hours) the media covering the cells in each well was removed and placed into new 96-well plates with appropriate labeling. These media plates were stored at −80° C. until needed for analysis.

Leakage of the GST enzyme is determined by collecting the media in which the cells were exposed to the test compound at the end of the 24 hour exposure period. Thus, GST values represent total GST lost over the exposure period. The control for 100% dead or maximum GST release is based on cells treated with 1 mM digitonin at $T_0$. Percent dead cells relative to digitonin treated cells was determined and then subtracted from 100 to yield the percent live cells.

Mitochondrial Function Assay (3-(4,5-dimethylthiazol-2-yl)-2,5-diphenyl-tetrazolium bromide (MTT). After the media was removed from a plate for GST analysis, the cells remaining in each well were evaluated for their ability to reduce the tetrazolium dye to formazan via mitochondrial dehydrogenase activity. An MTT stock solution was prepared in Earl's Buffered Salt Solution (EBSS) to a final concentration of 5.0 mg/ml. This stock was diluted 10-fold with complete media (0.5 mg/ml) just prior to use and warmed to 37° C. in a water bath. In some instances the MTT powder may be added directly to complete medium to give a final concentration of 0.5-mg/ml. Once the media was removed from all wells 200 microliter, of the 0.5 mg/ml MTT solution was added to each well and the plate was allowed to incubate at 37° C. for 3–4 hours. Color development is linear over this time.

After the 3–4 hour incubation, all media was removed and the purple formazan product was extracted by adding 200 microliters, of anhydrous isopropanol. The plates were covered with foil and placed on an orbital shaker for 30 min at room temperature. Each well was aspirated with a multichannel pipette to insure solubilization of the formzan dye and then the plate was centrifuged at 3000 rpms in a Beckman Allegra 6R centrifuge equipped with a GH3.8 rotor to remove insoluble cellular debris. Analyses were performed by transferring 100 microliters, of supernatant to a clean 96-well plate and then reading the sample absorbance at 570 nm and the reference absorbance at 650 nm with a Packard scanning spectrophotometer.

At the end of the 24 hour exposure period the media was removed and the remaining attached cells were assayed for mitochondrial function. Cells with viable mitochondria will have the greatest amount of MTT activity and hence the highest absorbance values. Percent control values were determined by dividing the mean absorbance of the treatment group by the mean absorbance of the control group and multiplying by 100.

Cell Proliferation (CYQUANT®) Assay

Cell number in each well was determined with the CYQUANT® cell proliferation kit from Molecular Probes. This assay is based on a DNA-specific binding dye that fluoresces upon interaction with DNA. Conversion to cell number is achieved by comparing sample fluorescence units to a standard curve based on fluorescence units/cell. The assay was performed essentially as described by the manufacturer with the following exceptions: The digitonin (1 mM) or Triton X 100 (1%) was added to the lysis buffer. The lysis buffer was added to the plates immediately after removing the plates from the −80° C. freezer. The plates were shaken for 20 min prior to reading the fluorescence. Maximum storage time at −80° C. without a significant loss in signal was determined to be no longer than 7 days.

Cell number was determined by establishing a calibration curve. In order to obtain fluorescence units (FU) per cell $1 \times 10^6$ cells were placed in a tube and centrifuged to a pellet. The pellet was then resuspended in 1 milliliters of a cell lysis buffer containing the DNA binding dye. Thus, one million cells in 1000 milliliters yields a relationship of 1000 cells per microliter of suspension. This provides FU/cell. Cell number for samples was determined by applying the FU obtained to the calibration curve. The percent change relative to controls was determined by dividing the treatment cell number by the control cell number and multiplying by 100.

ATP Assay

Cellular Adenosine triphosphate (ATP) was determined with the ATP-Lite kit from Packard Instruments according to the manufacturer's instructions. This assay is based on a reaction between ATP+D-luciferin+oxygen catalyzed by luciferase to yield Oxyluciferin+AMP+PPi+$CO_2$+light. The emitted light is proportional to the amount of ATP present. Rather than a "flash" type signal which has a very short half-life, this assay utilizes a "glow" technology that extends the signal half-life to 5 hours. In addition, a unique cell lysis reagent inhibits endogenous ATPases and therefore stabilizes cellular ATP by preventing its degradation to ADP.. ATP is present in all living cells and declines rapidly upon cell death. In addition, this assay in combination with the MTT assay provides an indicator of mitochondrial activity and the energy status of the cell.

Changes in ATP may be expressed as a percent change relative to controls by dividing the mean treatment luminescence values by the control values and multiplying by 100. An actual amount of ATP can also be determined by including an ATP calibration curve in the assay and then converting the luminescence response to an ATP concentration with the regression coefficients. Finally, it is possible to estimate the amount of ATP produced per cell, by dividing the pmol ATP data by cell number. Typically, cells try to maintain a stable level of ATP and therefore this parameter is not routinely calculated unless information on the stability of the ATP pool is desired.

EXAMPLE 2

Ketoconazole: A drug of limited toxicity as determined by CATS

In this Example, ketoconazole was used as the test drug. Rat hepatoma cells were seeded into 96-well culture plates and allowed to establish growth for 48 hours. Following this growth phase, the cells were treated with 0, 0.05, 0.1, 1, 5, 10, 20, 50, 100, and 300 micromolar of ketoconazole in growth medium and 0.5% DMSO. After a 24 hour exposure period, the cells and surrounding media were analyzed as described in Example 1.

Figure 4:
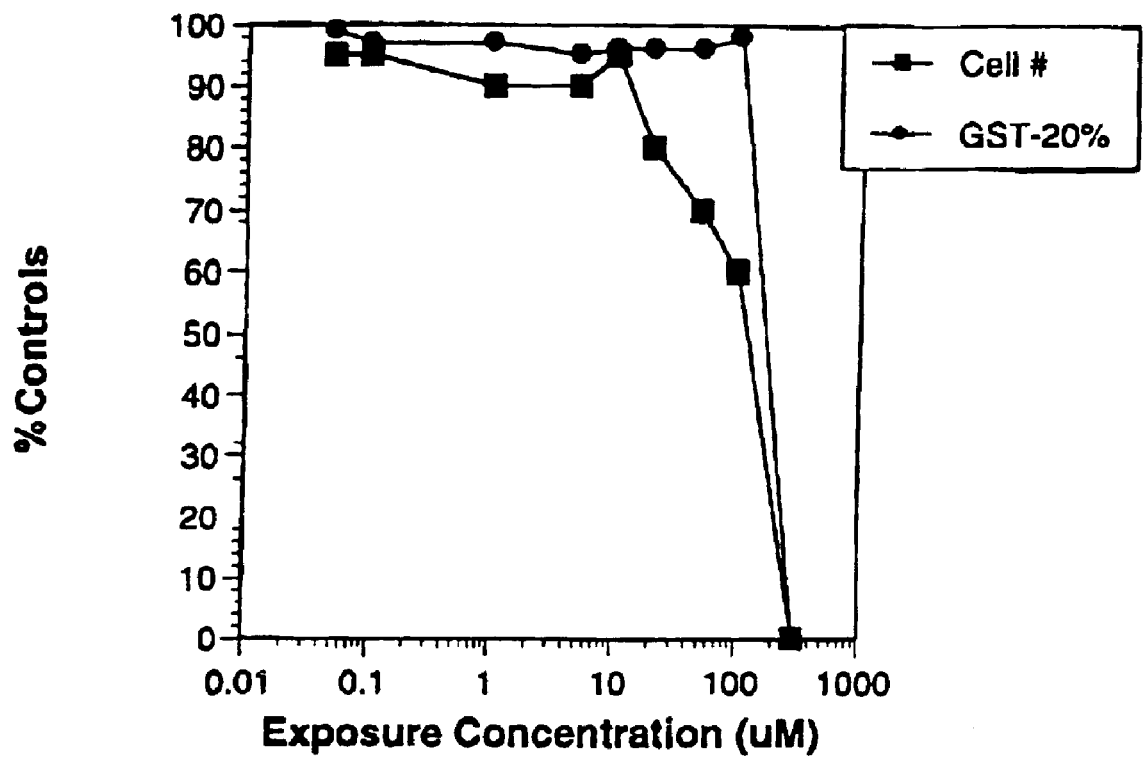
FIG. 4 is a graph which shows a dose response effect of ketoconazole on both cell number and the release of GST.
Figure 5:
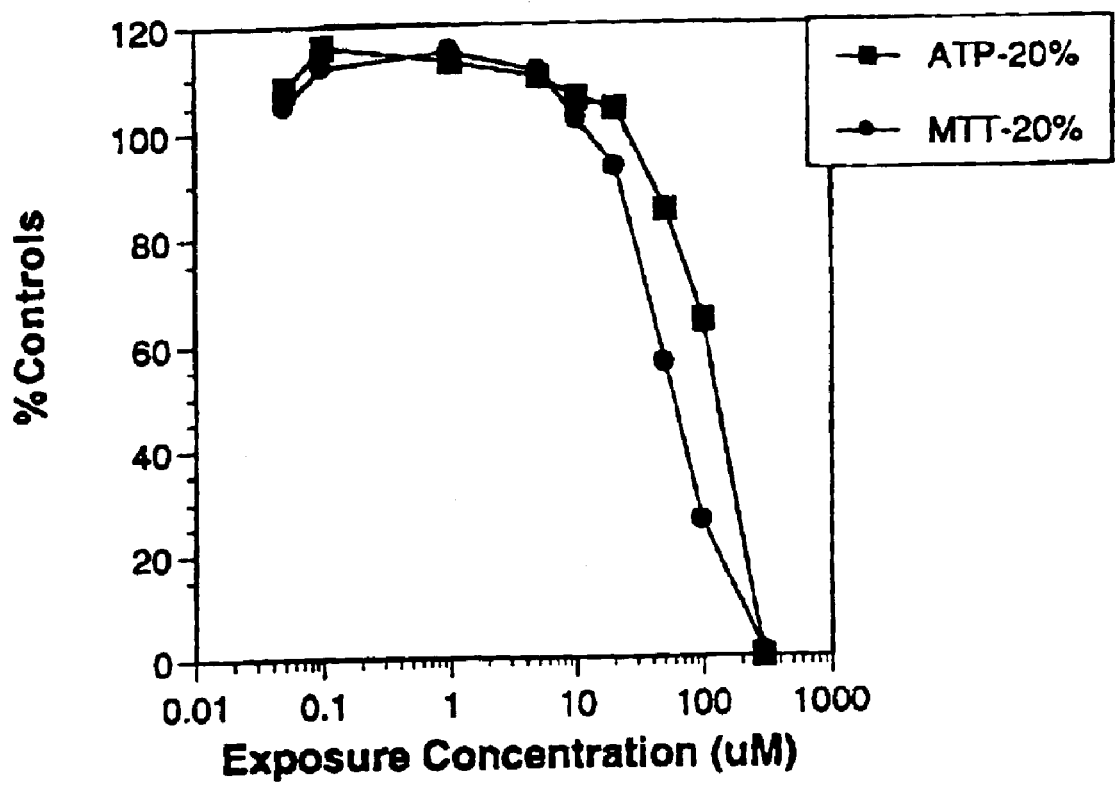
FIG. 5 is a graph which shows a dose response effect of ketoconazole in MTT or ATP assays to monitor mitochondrial function alone.
Figure 6A:
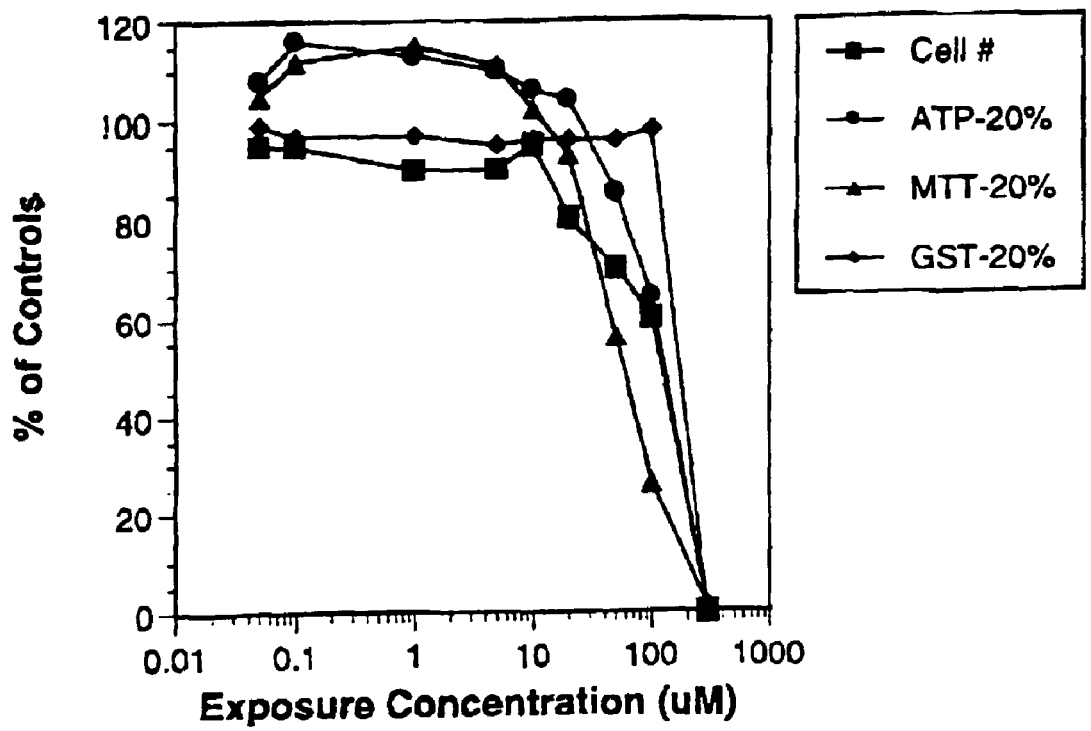
FIG. 6A and 6B are graphs which show that CATS analysis provides a good estimate of in vivo toxicity using ketoconazole as an example.

The effects of varying ketoconazole concentration was determined by measuring cell number (FIG. 2), GST leakage (FIG. 3), both cell number and the release of GST (FIG. 4), and an MTT assay or ATP assay (FIG. 5). Data from the cell number, GST leakage, MTT and ATP assays were combined to reveal a more complete picture of ketoconazole toxicity (FIG. 6A).

Figure 2:
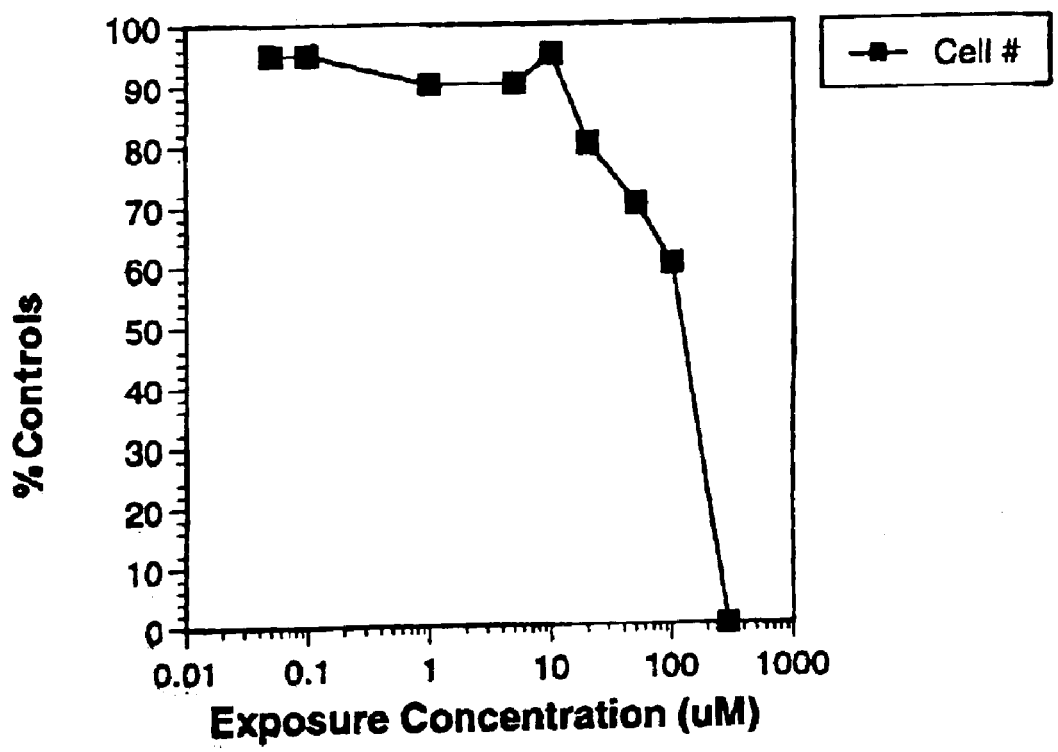
FIG. 2 is a graph which shows a dose response effect of ketoconazole on cell number using a CYQUANT® assay.
Figure 3:
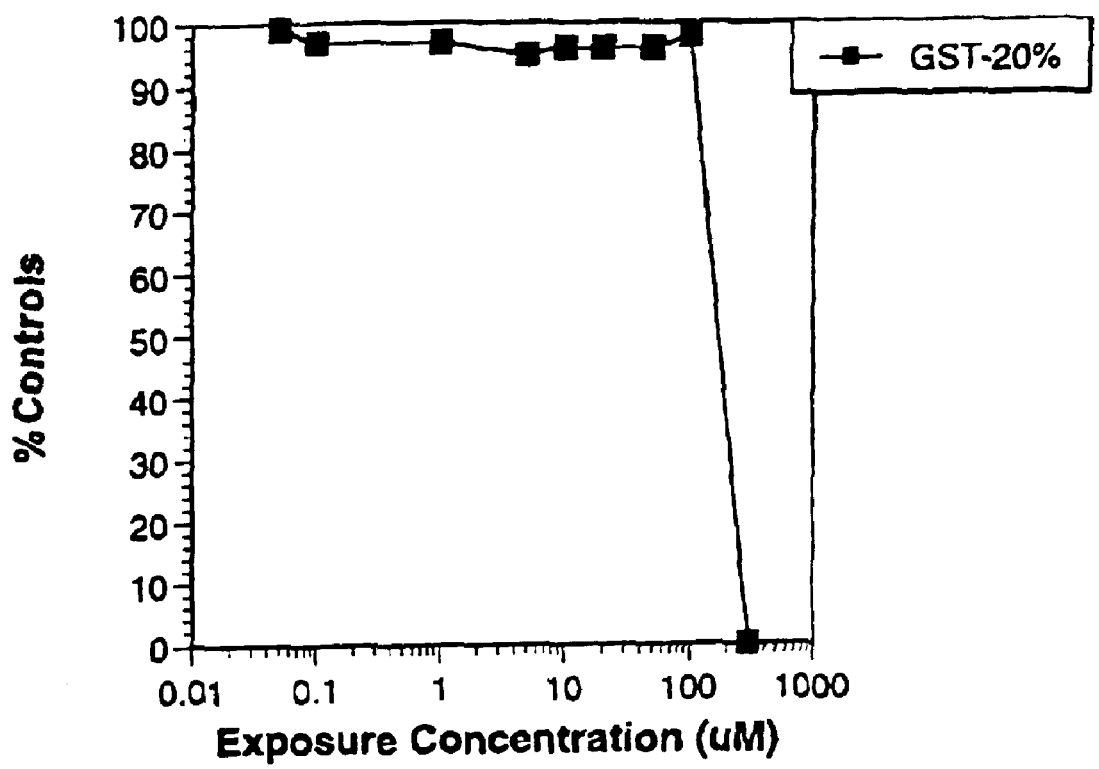
FIG. 3 is a graph which shows a dose response effect of ketoconazole on a standard GST leakage assay to monitor membrane integrity.

If only cell number was monitored for this compound the effect would be a dose-related reduction in cell number seen in FIG. 2. These data alone leaves many questions. Is cell number reduced because of cell death or is cell number (relative to controls) appearing to decrease, but in actuality the cells have simply stopped replicating? On the other hand, if a standard enzyme leakage assay had been used to monitor cell death (e.g., LDH or GST) the results would suggest that ketoconazole was not toxic to cells below 300 micromolar (FIG. 3). However, when the two assays are run together, more useful information is obtained. In this case cell number is decreasing without a concomitant increase in the release of GST (FIG. 4). Therefore, the reduction in cell number is due to reduced replication and not cell death. If MTT or ATP had been performed without the preceding information, the conclusion would be that ketoconazole is toxic with early effects observed below 20 micromolar (FIG. 5). Again, the reduction in ATP/MTT assays could be due to acute cytotoxicity (dead cells), reduced rate of replication or direct effects on mitochondrial function. When all four assays are viewed together a more complete picture of ketoconazole toxicity is revealed (FIG. 6A).

Ketoconazole inhibits mitochondrial function and reduces ATP levels prior to producing an inhibitory effect on cell replication. The reduction in cellular ATP signals a stress situation and the cell goes into Go or resting stage to conserve energy. This in turn results in an apparent decrease in cell number relative to controls. Thus, combining all these data yields a powerful mechanism for the prediction of toxicity.

Cell number is an indication of cell proliferation or cell death. If cell numbers relative to controls decrease with increasing exposure with a concomitant release in a marker enzyme such as GST, then the reduction in cell numbers can be attributed to cell death. If on the other hand cell numbers decrease in the absence of GST release the compound may be affecting the cells ability to replicate, without producing overt cytotoxicity. A reduction in MTT activity can be the result of cell death, inhibition of mitogenesis, or a direct mitotoxic effect. If a test compound produced a decrease in cell number and MTT activity, but not an increase in GST leakage, the compound may be inhibiting cell replication or mitogenesis.

If the exposure concentration that yields a half-maximal response ($TC_{50}$) for MTT activity is lower than the $TC_{50}$ for a reduction in cell number, then the compound may be directly inhibiting mitochondria which leads to reduced cell number and ultimately cell death and GST leakage. Thus, by carefully evaluating the response profiles of each assay and by knowing the specific endpoints being measured and how they can be affected it is possible to develop sound predictions on potential mechanisms of cytotoxicity.

Figure 6B:
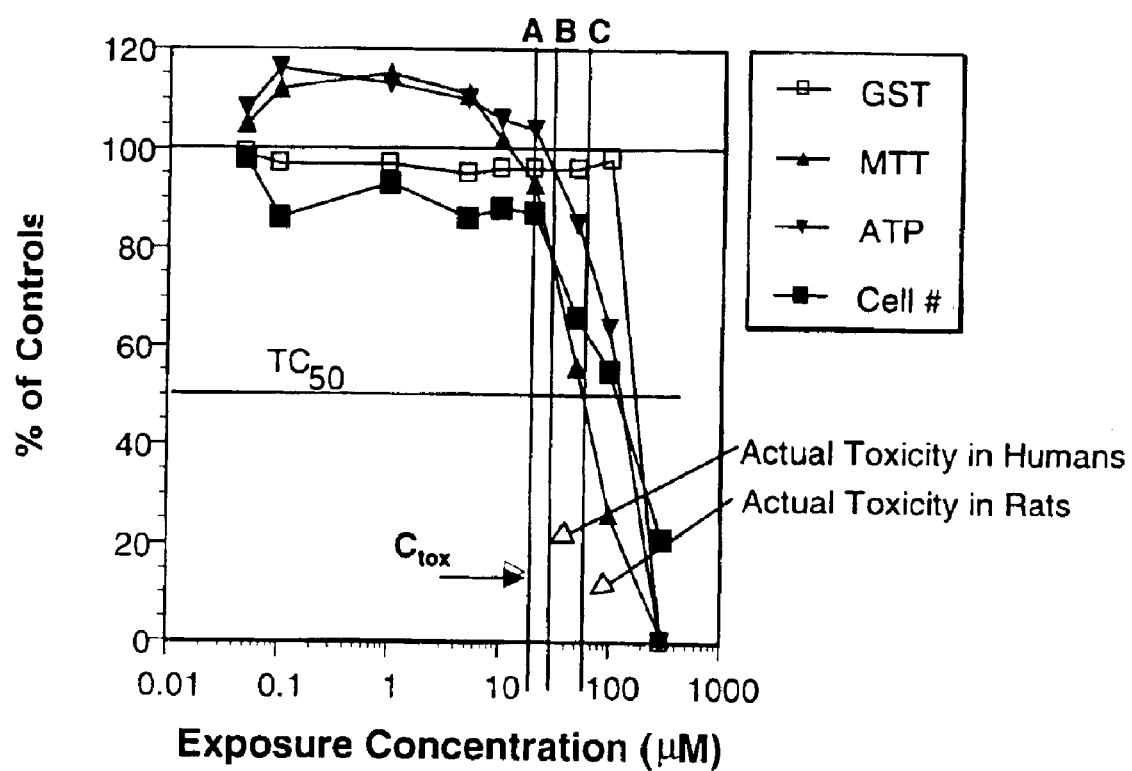

Ketoconazole is an antifungal agent and the first in its class to be used clinically. This drug is generally well tolerated in humans under normal dosing regimens. However, high doses over prolonged periods of treatment can result in toxicity associated with the liver, adrenals, and testes. The liver rapidly metabolizes ketoconazole and toxicity is believed to be associated with the parent compound. In the CATS system, compounds with $TC_{50}$ values greater than or equal to 50 micromolar do not exhibit severe hepatic toxicity in vivo. CATS analysis of ketoconazole revealed that all parameters measured had $TC_{50}$ values greater than or equal to 50 micromolar. These data are consistent with the fact that ketoconazole possesses low hepatic toxicity under normal treatment regimens. When ketoconazole is used at higher doses over prolonged periods of time, liver toxicity can ensue. In rats, plasma concentrations sustained at 60 micromolar produce hepatic damage (line C in FIG. 6B). In humans, a plasma concentration sustained at 30 micromolar has resulted in liver toxicity (line B in FIG. 6B). CATS analysis estimated the plasma concentration ($C_{tox}$) that would produce toxicity at 20 micromolar (line A in FIG. 6B). The mechanism(s) of ketoconazole mediated hepatotoxicity is in part due to inhibition of mitochondrial function as demonstrated by direct inhibition of State III respiration in isolated mitochondria. CATS analysis revealed that indeed ATP and MTT were reduced followed by reduction in cell replication (no GST leakage) which eventually resulted in cell death at the highest exposure concentrations (complete GST leakage) (FIG. 6A and FIG. 6B).

These data demonstrate the usefulness of CATS analysis in the drug discovery process. Ketoconazole would not have been dropped from development due to toxicity because the $TC_{50}$ values were equal to or greater than 50 µM, and under most dosing scenarios, plasma concentrations would not reach $C_{tox}$ levels. In addition, CATS provided information on potential targets of toxicity (mitochondria), and a good estimate of the plasma concentration in vivo that would result in toxicity ($C_{tox}$).

EXAMPLE 3

Comparison of toxicity of three antifungal compounds with ketoconazole

In this Example, the toxicity profiles of three azole antifungal compounds generated using the toxicity cluster analysis are compared to each other and to the well known antifungal drug, ketoconazole.

In the present Example, the effects of various concentrations of these three compounds were monitored using cell number, MTT, ATP, and GST leakage assays. The individual assays were conducted essentially as described above in Example 1. In the graph labeled "High Toxicity", all four biochemical endpoints were affected in the same manner and magnitude with a $TC_{50}$ near 10 micromolar (FIG. 9). In the graph labeled "Low Toxicity" the test compound had no effect on any of the assays evaluated (FIG. 10). In comparison, the data collected for a third compound presented in the graph labeled "Potentially Toxic-Unique Mechanism" only the ATP assay responded in a clear concentration dependent manner (FIG. 11).

These data indicate a potentially toxic compound with a unique mechanism. The test compound is altering an important biochemical pathway (ATP or energy) but this effect has not resulted in acute toxicity under the experimental conditions used in the cluster analysis. This does not mean however, that toxicity would not ensue given an altered experimental paradigm, such as an extended exposure time.

When these compounds are compared to ketoconazole additional information can be obtained. For example, the compound listed as toxic in FIG. 9 has $TC_{50}$ values of approximately 10 micromolar, while ketoconazole's $TC_{50}$ values are 70 micromolar for MTT and greater than 100 micromolar for all other endpoints. Thus, ketoconazole is considered less toxic than the other azole antifungal.

A single toxicity assay would not have provided the same information. For example, in the "High Toxicity" graph (FIG. 9), if cell number had been the only assay used, it would not be clear whether the decrease in cell number was due to acute cytotoxicity (cell death) or simply a reduction in the replication of cells, two very different conclusions. Similarly, if MTT or ATP had been run alone, it would not be clear whether the decrease was related to reduced cell numbers (either by death or by reduced replication) or to a direct effect on mitochondrial function (FIG. 9).

When GST is part of the profile it becomes clear that the effects on the other parameters are due to acute cytotoxicity resulting in cell death (FIG. 9). The fact that all the dose-response curves can be overlaid and produce a profile that responds to the compound exposure concentration uniformly in each assay suggests that they are all being affected by the same event, cell death. If MTT or ATP had responded at lower doses prior to changes in GST leakage, then information on preceding events that lead to toxicity could be obtained. An example of this scenario can be seen in the FIG. 11 which depicts a concentration-related reduction in ATP without changes in any of the other parameters.

Figure 8:
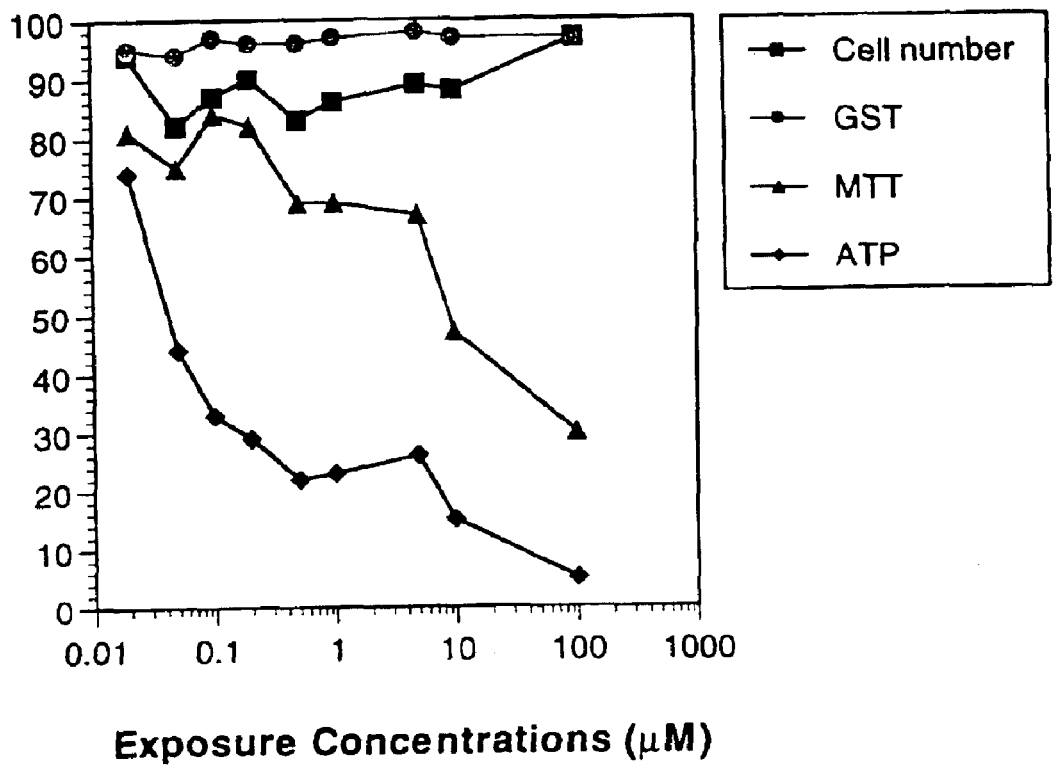
FIG. 8 is a graph which shows the results of CATS analysis performed for the compound oligomycin.

These data indicate a direct effect on ATP synthesis or on mitochondrial membrane permeability (uncoupling). MTT has not been affected because MTT reduction in the mitochondria occurs at complex I and II of the oxidative phosphorylation chain. ATP synthesis occurs at complex V. An example chemical that would result in a similar effect is oligomycin (FIG. 8), which specifically targets ATP synthase at complex V. After a 6 hour exposure to oligomycin, cell number, and GST are unaffected. MTT is significantly reduced but ATP is completely depleted. FIG. 8 shows that nearly all the ATP has depleted prior to any significant changes in MTT. In this example, if a GST or cell number assay had been used, the compound would appear to be non-toxic, however, by including markers for key biochemical processes, such as ATP for mitochondrial function, the cytotoxicity is revealed.

EXAMPLE 4

Rotenone: An example of a very toxic drug as investigated by CATS

Figure 7:
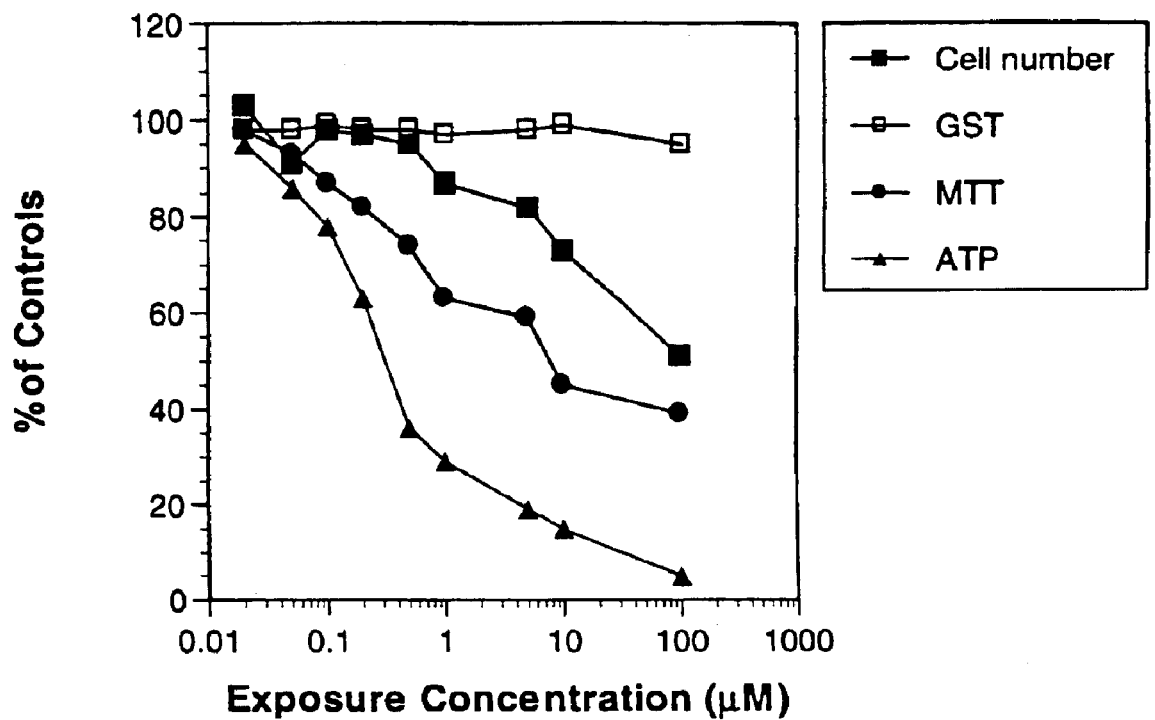
FIG. 7 is a graph which shows the results of CATS analysis performed for the compound rotenone.

Another example of why multiple assays that measure key cell biochemical processes (CATS) provide the most complete picture can be seen in FIG. 7 which depicts, the effects of various concentrations of rotenone on cell number, MTT, ATP, and GST leakage assays. The assays were performed as described in Example 1.

Rotenone is a well-studied chemical that specifically blocks mitochondrial oxidative phosphorylation and hence the synthesis of ATP at complexes I and I. This compound is extremely toxic to mammals, yet if the GST assay had been the only assay used in a 6 hour exposure in vitro, no toxicity would have been detected. However, when the entire cluster of assays is evaluated it is clear that one of the earliest events is depletion of ATP. ATP, MTT and Alamar blue were all decreased, however, the next most sensitive marker was ATP. Cell number is decreased, but this is due to reduced replication and not cell death (no GST leakage). One of the most energy dependent processes that occurs in a cell is replication. Therefore, depletion of ATP, and altered mitochondrial function would result in a decreased capacity to replicate and a reduction in cell number at higher doses. Longer exposures would result in cell death and an increase in GST leakage. These data also indicate that low exposures for prolonged periods could also be toxic to cells.

EXAMPLE 5

Detection of Toxicity in Proliferating Cell Populations

The present example shows how CATS analysis can be used to detect compounds that are toxic primarily to proliferating cell populations as seen in FIG. 13A–B and FIG. 14A–D.

Figure 13A:
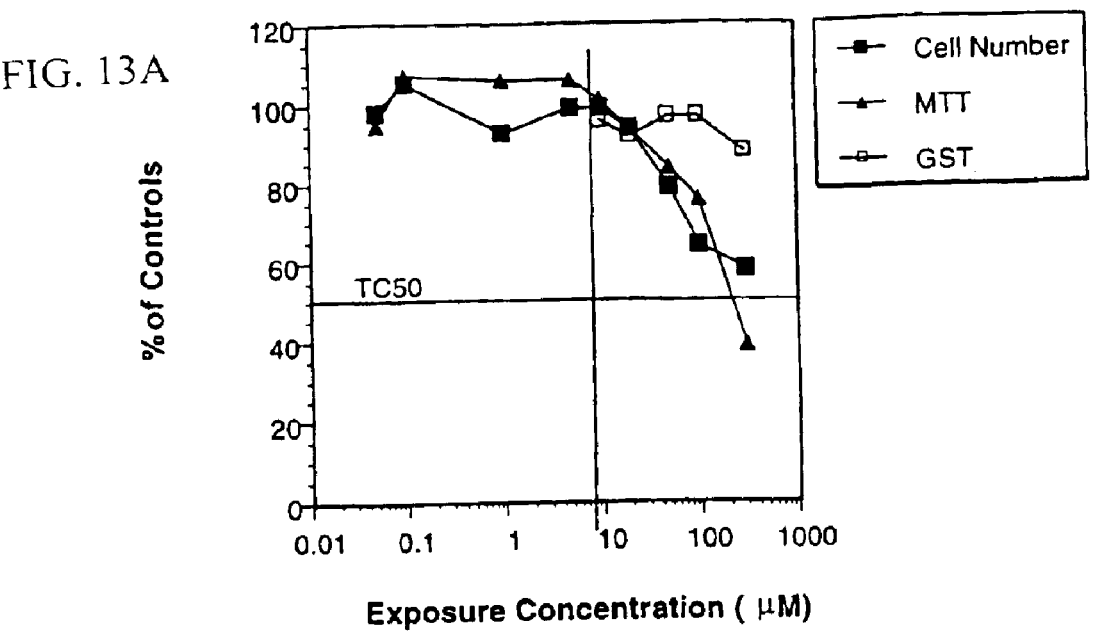
FIG. 13A and FIG. 13B are graphs which demonstrate the detection of toxicity in proliferating cell populations.
Figure 13B:
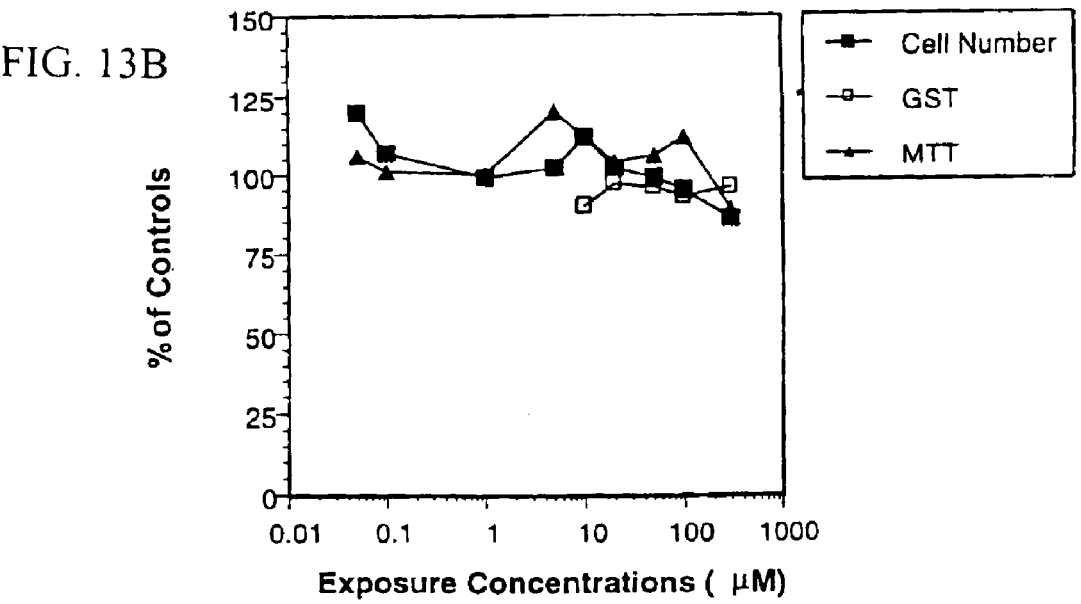

FIG. 13A shows the effects of compound A on general cell health following a 24 hour exposure and FIG. 13B shows the effects of compound B on general cell health following a 24 hour exposure when the compounds are evaluated in the standard CATS analysis. Both of these compounds are examples of compounds that produce significant hypocellularity in bone. Compound A is considerably more toxic than compound B.

FIG. 13A shows a modest concentration dependent reduction in cell number and MTT, without any change in GST in cells exposed to compound A. In contrast compound B had essentially no effect. For compound A, the pattern of reduced cell number at higher doses and reduced mitochondrial function appeared to indicate toxicity to mitochondria, proliferating cells or both.

Figure 14A:
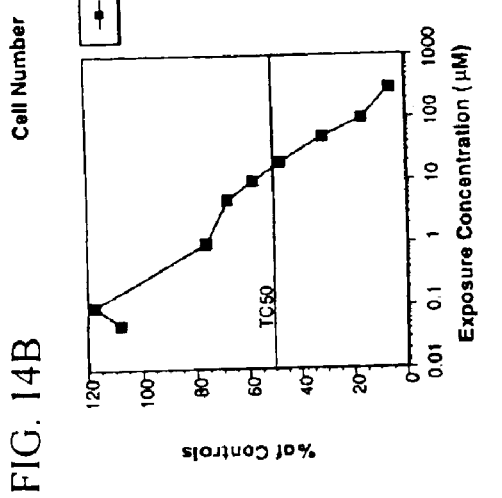
FIG. 14A–FIG. 14D are graphs which show toxicity in proliferating cell populations mediated by compound A is time dependent.
Figure 14B:
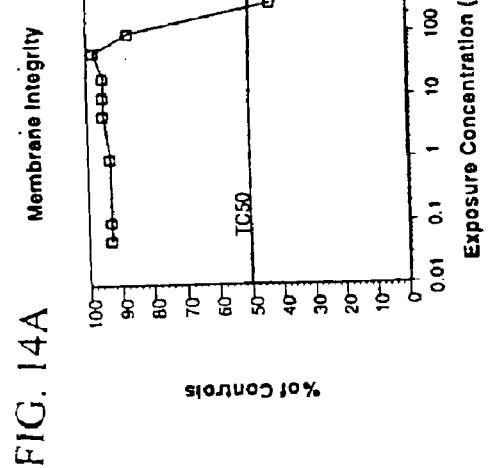
Figure 14C:
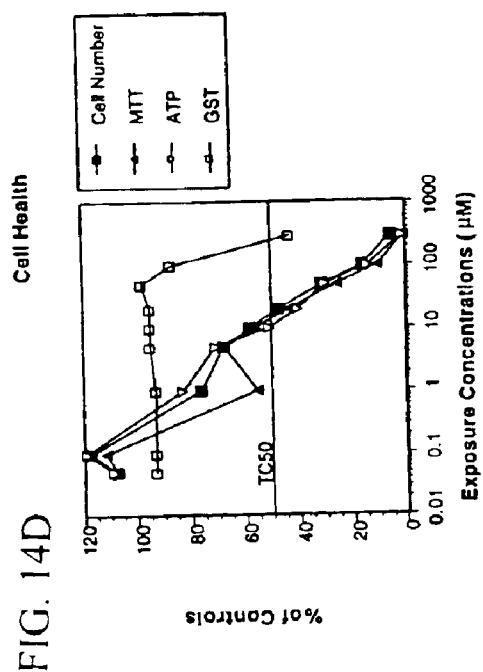
Figure 14D:
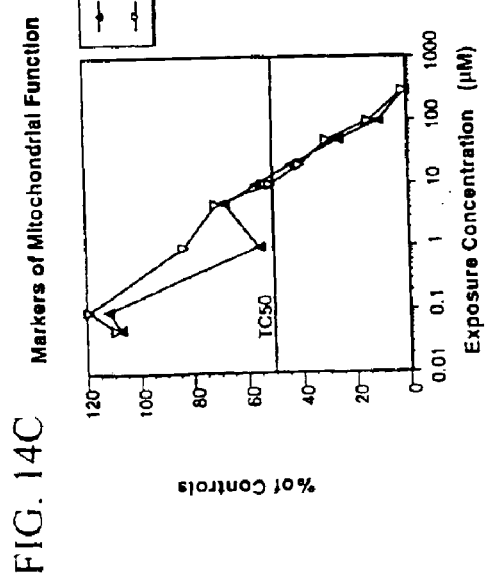

To evaluate the hypothesis that toxicity to proliferating cells may require population doublings in order to accurately predict the toxicity, compound A N1 was submitted to another CATS analysis for 72 hours rather than the standard 24 hours. The results are show in FIG. 14A–FIG. 14D. After 72 hours of exposure there was essentially no acute cytotoxicity at the low exposures as determined by a GST assay (FIG. 14A). Cell number however, showed a marked concentration dependant reduction (FIG. 14B) as did the mitochondrial markers MTT and ATP (FIG. 14C). FIG. 14D represents all the endpoints placed on one graph. It is clear that compound A has a dramatic effect on proliferating cells that results in an inability of cells to replicate which is most likely die to altered mitochondrial function. A greater resolution between endpoints was achieved by performing the CATS analysis at time points between 24 and 72 hours.

The data in this example show that CATS toxicity profiled at 24 hours are useful in: predicting toxicity of proliferating cells, such as bone marrow cells.

While the methods and compositions herein have been described in terms of preferred embodiments, it will be apparent that variations may be applied to the methods and/or compositions without departing from the concept, spirit and scope of the invention. More specifically, it will be apparent that assays which are physiologically related may be substituted for the assays described herein while still producing the same or similar results. All such similar substitutes and modifications apparent to those of skill in the art are deemed to be within the scope of the invention as defined by the appended claims.

To the extent that certain exemplary procedural or other details supplementary to those described herein may be found in the references cited herein, such references are all specifically incorporated herein by reference.

What is claimed is:

1. A method of determining a level of toxicity of a chemical compound comprising:
   a) culturing cells in the presence of a plurality of concentrations of said chemical compound;
   b) measuring a first indicator of cell health at four or more concentrations of said chemical compound;
   c) measuring a second indicator of cell health at four or more concentrations of said chemical compound;
   d) measuring a third indicator of cell health at four or more concentrations of said chemical compound;
   e) determining the level of toxicity of said chemical compound from the measurements taken in steps (b), (c) and (d) by
      i) performing a dose response analysis of for each indicator of cell health from the measurements taken in steps (b), (c) and (d);

ii) identifying, from the dose response analyses, the highest concentration of said chemical compound at which no measurable toxic effect was observed for each measured indicator of cell health;

iii) selecting, as the toxic concentration ($C_{tox}$), a concentration less than or equal to the highest concentration of said chemical compound at which no measurable toxic effect was observed for all measured indicators of cell health, as a level of toxicity for the chemical compound.

2. The method of claim 1, wherein each said first, second and third indicators is independently selected from the group consisting of indicators of cellular replication, indicators of mitochondrial function, indicators of intracellular energy balance, indicators of cell membrane integrity and indicators of cell mortality.

3. The method of claim 1, further comprising determining a concentration of said compound that produces a half maximal toxic effect ($TC_{50}$) for each of said indicators of cell health.

4. The method of claim 1, wherein said plurality of concentrations are selected from a concentration range from 0 micromolar and to about 300 micromolar.

5. The method of claim 1, wherein step (i) comprises plotting the measurements for each said cell health indicators on a graph as a function of concentration for each said cell health indicators of the chemical compound.

6. The method of claim 5, wherein the measurements of each of said cell health indicators are expressed relative to a control measurement as a function of concentration of the chemical compound.

7. The method of claim 6, wherein the measurements of all of said cell health indicators are plotted on a single graph.

8. The method of claim 1, wherein at least one of said cell health indicators is measured from the supernatant of said cell culture.

9. The method of claim 8, wherein at least one of said cell health indicators is measured from cellular components of said cell culture.

10. The method of claim 1, wherein said first health indicator monitors cellular replication, said second cell health indicator monitors mitochondrial function, and said third cell health indicator monitors membrane integrity.

11. The method of claim 10, wherein cellular replication is monitored with an assay selected from the group consisting of an assay that measures $^3$H-thymidine incorporation; a BrdU incorporation assay, or a DNA binding assay.

12. The method claim 11, wherein said mitochondrial function is monitored with an assay selected from the group consisting of an ATP assay, an MTT assay, an Alamar Blue assay, and a Rhodamine 123 assay.

13. The method of claim 12, wherein said membrane integrity is monitored with an assay selected from the group consisting a glutathione S-transferase assay, lactate dehydrogenase assay, aspartyl aminotransferase assay, alanine aminotransferase assay, isocitrate dehydrogenase assay, sorbitol dehydrogenase assay, glutamate dehydrogenase assay, ornithine carbamyl transferase assay, γ-glutamyl transferase assay, and alkaline phosphatase assay.

14. The method of claim 13, further comprising measuring a fourth cell health indicator selected from the group consisting of indicators of cellular replication, indicators of mitochondrial function, indicators of intracellular energy balance, indicators of cell membrane integrity and indicators of cell mortality.

15. The method of claim 14, wherein said fourth indicator of cell health is an indicator of energy balance that is measured with an assay selected from the group consisting of an ATP/ADP balance assay and oxygen consumption assay.

16. The method of claim 14, wherein the fourth indicator of cell health is a cell mortality assay selected from the group consisting of cell number assay and an apoptosis assay.

17. The method of claim 14, further comprising measuring a fifth cell health indicator selected from the group consisting of indicators of cellular replication, indicators of mitochondrial function, indicators of intracellular energy balance, indicators of cell membrane integrity and indicators of cell mortality.

18. The method of claim 1, wherein said cells are primary cells.

19. The method of claim 1, wherein said cells are of mammalian origin and are selected from the group consisting of liver cells, kidney cells, brain cells, fibroblast cells, nerve cells, skin cells, lung cells, spleen cells, endometrial cells, cardiac cells, stomach cells, breast cells, stem cells and a hematopoietic cell; and cell lines derived from any of these cells.

20. The method of claim 1, wherein said cells are from a mammalian cell line.

21. The method of claim 20, wherein said cells are liver cell line cells.

22. The method of claim 21, wherein said liver cells are human liver cell line cells.

23. The method of claim 21, wherein said liver cells are rodent liver cell line cells.

24. The method of claim 1, wherein said chemical compound is selected from the group consisting of an antimicrobial agent, an antitumor agent, an immunomodulator, a neurotransmitter, an agent for treatment or prevention of a central nervous system disease or disorder or cardiovascular disease or disorder; and an anti-inflammatory agent.

* * * * *